US012364563B2

(12) United States Patent
Torabi

(10) Patent No.: US 12,364,563 B2
(45) Date of Patent: *Jul. 22, 2025

(54) DEEP DISENGAGEMENT DETECTION DURING TELESURGERY

(71) Applicant: Verb Surgical Inc., Santa Clara, CA (US)

(72) Inventor: Meysam Torabi, Union City, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/676,049

(22) Filed: May 28, 2024

(65) Prior Publication Data

US 2024/0307143 A1  Sep. 19, 2024

Related U.S. Application Data

(63) Continuation of application No. 17/030,182, filed on Sep. 23, 2020, now Pat. No. 12,029,522.

(51) Int. Cl.
*A61B 34/35* (2016.01)
*A61B 34/00* (2016.01)
(Continued)

(52) U.S. Cl.
CPC .............. *A61B 34/75* (2016.02); *A61B 34/25* (2016.02); *A61B 34/35* (2016.02); *A61B 34/74* (2016.02);
(Continued)

(58) Field of Classification Search
CPC ........... G06K 9/00281; G06K 9/00302; G06K 9/2081; G06N 3/08; G06N 3/044;
(Continued)

(56) References Cited

U.S. PATENT DOCUMENTS 6,728,599 B2  4/2004  Wang et al.
9,717,563 B2  8/2017  Tognaccini et al.
(Continued)

FOREIGN PATENT DOCUMENTS

KR  10-1802464 B1  11/2017
WO  2018/074715 A1  4/2018
(Continued)

OTHER PUBLICATIONS

Choi et al., Surgical-tools detection based on Convolutional Neural Network in laparoscopic robot-assisted surgery, 2017, IEEE, p. 1756-1759 (Year: 2017).*

(Continued)

*Primary Examiner* — Mcdieunel Marc
(74) *Attorney, Agent, or Firm* — Aikin & Gallant, LLP

(57) ABSTRACT

User input device (UID) disengagement-detection techniques based on real-time time-series data processing and deep learning. A long short-term memory (LSTM) network-based classifier is trained based on the acquired time-series data of UID motions including both surgical motions and docking motions. The classifier is then used during teleoperation sessions to monitor the movements of UIDs, and continuously classify the real-time UID motions as either teleoperation motions or docking motions. The disengagement-detection techniques can immediately disengage the UIDs from the surgical tools as soon as the monitored UID motions are classified as docking motions, thereby preventing unintended surgical tool motions. The disclosed disengagement-detection techniques allow the UIDs and the surgical tools to become disengaged naturally by simply having the user place the UIDs back to their docking positions without having to take any additional actions. Other aspects are also described and claimed.

21 Claims, 11 Drawing Sheets

(51) Int. Cl.
*G06N 3/04* (2023.01)
*G06N 3/044* (2023.01)
*G06N 3/08* (2023.01)
*G16H 40/67* (2018.01)
*A61B 34/30* (2016.01)

(52) U.S. Cl.
CPC ............... *G06N 3/04* (2013.01); *G06N 3/044* (2023.01); *G06N 3/08* (2013.01); *G16H 40/67* (2018.01); *A61B 2034/301* (2016.02); *A61B 2034/302* (2016.02)

(58) Field of Classification Search
CPC ........... G06N 3/04; G06T 11/00; G06T 7/246; G06T 2207/20081; G06T 2207/20084; G06T 2207/30201; G06V 10/235; G06V 40/165; G06V 40/171; G06V 40/174; G06V 40/19; H04N 7/147; H04N 7/157; A61B 34/74; A61B 34/25; A61B 34/35; A61B 34/30; A61B 34/75; A61B 2034/301; A61B 2034/302; G16H 40/67; G16H 20/40
See application file for complete search history.

(56) References Cited

U.S. PATENT DOCUMENTS

| | | | | |
|---|---|---|---|---|
| 10,137,575 | B2* | 11/2018 | Itkowitz | B25J 9/1692 |
| 10,258,425 | B2 | 4/2019 | Mustufa et al. | |
| 10,507,066 | B2 | 12/2019 | Dimaio et al. | |
| 10,603,127 | B2 | 3/2020 | Hasser et al. | |
| 10,820,949 | B2 | 11/2020 | Prisco et al. | |
| 11,197,731 | B2 | 12/2021 | Hoffman et al. | |
| 11,259,870 | B2 | 3/2022 | Dimaio et al. | |
| 11,439,472 | B2* | 9/2022 | Prisco | A61B 34/37 |
| 11,517,383 | B2* | 12/2022 | Abbott | A61B 34/35 |
| 11,638,622 | B2* | 5/2023 | Mustufa | A61B 90/36 600/102 |
| 11,648,059 | B2* | 5/2023 | Culman | A61B 34/35 703/11 |
| 2004/0024387 | A1* | 2/2004 | Payandeh | A61B 90/11 606/1 |
| 2008/0147089 | A1 | 6/2008 | Loh et al. | |
| 2009/0088775 | A1* | 4/2009 | Swarup | A61B 34/71 700/264 |
| 2011/0023285 | A1* | 2/2011 | Cooper | A61B 34/30 29/428 |
| 2012/0071892 | A1 | 3/2012 | Itkowitz et al. | |
| 2018/0256235 | A1* | 9/2018 | Cohen | A61B 34/35 |

FOREIGN PATENT DOCUMENTS

| | | |
|---|---|---|
| WO | 2020/036786 A1 | 2/2020 |
| WO | 2020/139405 A1 | 7/2020 |

OTHER PUBLICATIONS

Bowyer et al., Active Constraints/Virtual Fixtures: A Survey, 2014, IEEE, p. 138-157 (Year: 2014).*

Leite et al., Autonomous disengagement classification and repair in multiparty child-robot interaction, 2016, IEEE, p. 525-532 (Year: 2016).*

Chen et al., Surgical instruments tracking based on deep learning with lines detection and spatio-temporal context, 2017, IEEE, p. 2711-2714 (Year: 2017).*

Brown et al., Using Contact Forces and Robot Arm Accelerations to Automatically Rate Surgeon Skill at Peg Transfer, 2017, IEEE, p. 2263-2275 (Year: 2017).

Despinoy et al., Unsupervised Trajectory Segmentation for Surgical Gesture Recognition in Robotic Training, 2016, IEEE, p. 1280-1291 (Year: 2016).

International Preliminary Report on Patentability received for PCT Patent Application No. PCT/IB21/058540, mailed on Apr. 6, 2023, 6 pages.

International Search Report and Written Opinion for International Application No. PCT/IB2021/058540 mailed Dec. 17, 2021, 10 pages.

Islam et al., Developing a real-time low-cost system for surgical skill training and assessment, 2013, IEEE, p. 1-4 (Year: 2013).

Xuet et al., Multimodal Human Hand Motion Sensing and Analysis—A Review, 2019, IEEE, p. 162-175 (Year: 2019).

* cited by examiner

DEEP DISENGAGEMENT DETECTION DURING TELESURGERY

CROSS-REFERENCE TO RELATED APPLICATION

This application is a continuation of U.S. patent application Ser. No. 17/030,182, filed Sep. 23, 2020, entitled "DEEP DISENGAGEMENT DETECTION DURING TELESURGERY," which is hereby incorporated by reference in its entirety.

TECHNICAL FIELD

The present disclosure generally relates to robotic surgical systems, and more specifically to systems, devices and techniques for automatically detecting and causing user disengagements from robotically-assisted surgical tools during robotic surgeries.

BACKGROUND

Endoscopic surgery involves looking into a patient's body and performing surgery inside the patient's body using endoscopes and other surgical tools. For example, laparoscopic surgery can use a laparoscope to access and view an abdominal cavity. Endoscopic surgery can be performed using manual tools and/or a robotic surgical system having robotically-assisted tools.

A robotic surgical system may be remotely operated by a surgeon to command a robotically-assisted surgical tool located at an operating table. Such operation of a robotically-assisted tool remotely controlled by a surgeon may be commonly referred to as teleoperation. For example, the surgeon may use a computer console located in the operating room, or it may be located in a different city, to command a robot to manipulate the surgical tool mounted on the operating table. The robotically-assisted tools can include an endoscope mounted on a robotic arm. Accordingly, the surgical robotic system may be used by the remote surgeon to perform an endoscopic surgery.

The surgeon may provide input commands to the robotic surgical system, and one or more processors of the robotic surgical system can control system components in response to the input commands. For example, the surgeon may hold in his/her hands one or two user input devices (UIDs) to generate control signals to cause motion of the robotic surgical system components, e.g., an actuator, a robotic arm, and/or a surgical tool of the robotic surgical system.

At the end of each teleoperation session, a user of the robotic surgical system often needs to disengage the UIDs from the surgical tools being controlled. Some existing techniques of user disengagement involve having the surgeon to clutch out by releasing a foot pedal. These user disengagement techniques require precise timing of the clutching out action and precise coordination between the hand motions and foot motions, which inevitably require the user to take additional trainings. Unfortunately, even after the training, it is possible that the user may forget to take the disengagement action in some actual operations by directly returning the UIDs to their docking positions. In such cases, the surgical tools remain engaged while the docking motions translate to the unintended movements of the surgical tools. If the surgical tools remain in the patient's body, such unintended movements can have serious consequences, such as causing injuries.

SUMMARY

Disclosed are various user input device (UID) disengagement-detection techniques based on real-time time-series data processing and deep learning. More specifically, various disclosed UID disengagement-detection techniques include training a recurrent neural network (RNN) such as a long short-term memory (LSTM) network-based classifier based on the acquired time-series data of UID motions including both surgical motions and docking motions. The trained deep-learning classifier can then be used during teleoperation sessions to monitor the movements of UIDs, and continuously classify the real-time UID motions as either teleoperation motions or docking motions. Hence, the disclosed UID disengagement-detection techniques can immediately cause the movements of robotic arms and surgical tools attached to the robotic arms to stop as soon as the monitored UID motions are classified as docking motions by the trained classifier, thereby preventing unintended surgical tool motions. The disclosed disengagement-detection techniques are fully automatic. In other words, the UIDs and the surgical tools can become disengaged naturally by simply having the user putting the UIDs back to their docking positions without having to remember to take any additional actions, while the docking motions of the UIDs are used by the trained classifier to automatically disengage the UIDs from the controlling the surgical tools.

In one aspect, a process for detecting a disengagement intention from a surgical tool in a robotic surgical system is disclosed. This process can begin by receiving a first time-series of positions of a first user input device controlling a movement of a first surgical tool and a second time-series of positions of a second user input device (UID) controlling a movement of a second surgical tool. Next, the process processes the first time-series and the second time-series to generate a plurality of derivative time-series of the first time-series and the second time-series. The process then applies a long short-term memory (LSTM) network classifier on the plurality of derivative time-series, wherein the LSTM network classifier is trained to detect disengagement and teleoperation motions of the first and second UIDs and generate either a disengagement decision or a teleoperation decision. In response to receiving a disengagement decision from the output of the LSTM network classifier, the process immediately disengages the first and second UIDs from controlling the first and second surgical tools.

In some embodiments, each of the first and second time-series of positions of the first UID and the second UID is a time-series of three-dimensional (3D) positions of a respective UID. The time-series of 3D positions further includes a first time-series of x-positions of the respective UID, a second time-series of y-positions of the respective UID, and a third time-series of z-positions of the respective UID.

In some embodiments, the process processes the first time-series and the second time-series to generate the plurality of derivative time-series by: (1) computing the derivative of the first time-series to generate a first derivative time-series of the first UID representative of a velocity of the first UID; and (2) computing the derivative of the second time-series to generate a second derivative time-series of the second UID representative of a velocity of the second UID.

In some embodiments, processing the first time-series and the second time-series to generate the plurality of derivative time-series further includes: (1) computing the derivative of the first derivative time-series to generate a third derivative time-series of the first UID representative of an acceleration of the first UID; and (2) computing the derivative of the second derivative time-series to generate a fourth derivative time-series of the second UID representative of an acceleration of the second UID.

In some embodiments, processing the first time-series and the second time-series to generate the plurality of derivative time-series further includes: (1) computing the derivative of the third derivative time-series to generate a five derivative time-series of the first UID representative of a jerk of the first UID; and (2) computing the derivative of the fourth derivative time-series to generate a sixth derivative time-series of the second UID representative of a jerk of the second UID.

In some embodiments, processing the first time-series and the second time-series to generate the plurality of derivative time-series further includes: (1) computing the derivative of the fifth derivative time-series to generate a seventh derivative time-series of the first UID representative of a snap of the first UID; and (2) computing the derivative of the sixth derivative time-series to generate a eighth derivative time-series of the second UID representative of a snap of the second UID.

In some embodiments, processing the first time-series and the second time-series to generate the plurality of derivative time-series further includes: (1) computing a ninth time-series by summing the first derivative time-series and the second derivative time-series representative of combined velocities of the first UID and the second UID; and (2) computing a tenth time-series by subtracting the first/second derivative time-series from the second/first derivative time-series representative of differences in velocities between the first UID and the second UID; (3) computing the derivative of the ninth time-series to generate a eleventh derivative time-series representative of a rate of change of the combined velocities; and (4) computing the derivative of the tenth time-series to generate a twelfth derivative time-series representative of a rate of change of the differences in velocities.

In some embodiments, processing the first time-series and the second time-series to generate the plurality of derivative time-series further includes: (1) computing the derivative of the eleventh derivative time-series to generate a thirteenth derivative time-series representative of a rate of change of the eleventh time-series; and (2) computing the derivative of the twelfth derivative time-series to generate a fourteenth derivative time-series representative of a rate of change of the twelfth time-series.

In some embodiments, processing the first time-series and the second time-series to generate the plurality of derivative time-series further includes: (1) generating a distance time-series by computing a set of distance values between each 3D-position in the first derivative time-series and a corresponding 3D-position in the second derivative time-series representative of distances between the first UID and the second UID; (2) computing the derivative of the distance time-series to generate a fifteenth derivative time-series representative of a rate of change of the 3D-distances between the first UID and the second UID; (3) computing the derivative of the fifteenth time-series to generate sixteenth derivative time-series representative of a rate of change of the fifteenth time-series; and (4) computing the derivative of the sixteenth time-series to generate seventeenth derivative time-series representative of a rate of change of the sixteenth time-series.

In some embodiments, the process applies the LSTM network classifier to the plurality of derivative time-series by first applying a sliding window of a predetermined window size to each of the plurality of derivative time-series to generate a composite data sample that includes a set of data points from each of the plurality of derivative time-series within the sliding window. The process next applies the LSTM classifier on the composite data sample to generate either a disengagement decision or a teleoperation decision based on the composite data sample.

In some embodiments, the plurality of derivative time-series include at least the velocities and accelerations of the first time-series and the second time-series. As such, applying the LSTM classifier on the plurality of derivative time-series allows for significantly reducing the predetermined window size to make each disengagement or teleoperation decision, thereby expediting the speed of disengagement detections and preventing unintended movements of the surgical tools.

In some embodiments, prior to applying the LSTM network classifier to the plurality of derivative time-series, the process trains the LSTM network classifier by receiving a first plurality of time-series of positions of a left UID and a second plurality of time-series of positions of a right UID. Next, for each time-series in the first plurality of time-series and a corresponding time-series in the second plurality of time-series, the process: (1) annotates the time-series to identify each teleoperation event in the time-series and each UID docking event in the time-series; and (2) processes the labeled time-series and the labeled time-series to generate a plurality of derivative time-series of the first time-series and the second time-series. The process subsequently uses the annotated and processed derivatives of first plurality of time-series and the second plurality of time-series as training data to train the LSTM network classifier.

In some embodiments, the process annotates the time-series to identify each teleoperation event in the time-series by: (1) identifying a first timestamp corresponding to the beginning of a teleoperation event and a second timestamp corresponding to the end of the teleoperation event; and (2) labeling each data point between the first timestamp and the second timestamp with a first value indicative of a teleoperation mode.

In some embodiments, the process annotates the time-series to identify each UID docking event in the time-series by: (1) identifying a third timestamp corresponding to the beginning of a UID docked mode; (2) labeling each data point between the second timestamp and the third timestamp with a second value indicative of a disengagement mode, the disengagement mode terminates when the UID docked mode begins.

In some embodiments, the disengagement motions include docking motions of returning the first and second UIDs to the respective docking stations.

In some embodiments, the LSTM network classifier includes a plurality of LSTM layers followed by a dropout layer with a dropout rate between 0.3-0.4, e.g., a dropout rate=0.3.

In another aspect, an apparatus for detecting a disengagement intention from a surgical tool in a robotic surgical system is disclosed. This apparatus includes one or more processors and a memory coupled to the one or more processors. The memory of the apparatus stores instructions that, when executed by the one or more processors, cause the apparatus to: receive a first time-series of positions of a first user input device controlling a movement of a first surgical tool and a second time-series of positions of a second user input device (UID) controlling a movement of a second surgical tool; process the first time-series and the second time-series to generate a plurality of derivative time-series of the first time-series and the second time-series; apply a long short-term memory (LSTM) network classifier on the plurality of derivative time-series, wherein the LSTM network classifier is trained to detect disengagement and teleoperation motions of the first and second UIDs and generate either a disengagement decision or a teleoperation decision; and in response to receiving a disengagement decision from the output of the LSTM network classifier, immediately disengaging the first and second UIDs from controlling the first and second surgical tools.

In yet another aspect, a robotic surgical system is disclosed. This robotic surgical system can include: a first and a second surgical tools; a first and a second user interface device (UID) for controlling movements of the first and the second surgical tools, respectively; and a computer coupled to the first and the second surgical tools and the first and the second UIDs. In some embodiments, the computer of the robotic surgical system is configured to perform real-time UID disengagement detections by: receiving a first time-series of positions of the first UID and a second time-series of positions of the second UID; processing the first time-series and the second time-series to generate a plurality of derivative time-series of the first time-series and the second time-series; applying a long short-term memory (LSTM) network classifier on the plurality of derivative time-series, wherein the LSTM network classifier is trained to detect disengagement and teleoperation motions of the first and second UIDs and generate either a disengagement decision or a teleoperation decision; and in response to receiving a disengagement decision from the output of the LSTM network classifier, immediately disengaging the first and second UIDs from controlling the first and second surgical tools.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Throughout the specification, the following terms have the meanings provided herein, unless the context clearly dictates otherwise. The term "docking" generally refers to a user-performed action of moving a left user input device (UID) and a right UID from the initial teleoperation locations to their respective docking positions. The term "disengagement" generally refers to a process of disabling UIDs from controlling the movements of the robotic arms and/or surgical tools.

Disclosed are various UID disengagement-detection techniques based on real-time time-series data processing and deep learning. More specifically, various disclosed UID disengagement-detection techniques include training a recurrent neural network (RNN) such as a long short-term memory (LSTM) network-based classifier based on the acquired time-series data of UID motions including both surgical motions and docking motions. The trained deep-learning classifier can then be used during teleoperation sessions to monitor the movements of UIDs, and continuously classify the real-time UID motions as either teleoperation motions or docking motions. Hence, the disclosed UID disengagement-detection techniques can immediately cause the movements of robotic arms and surgical tools attached to the robotic arms to stop as soon as the monitored UID motions are classified as docking motions by the trained classifier, thereby preventing unintended surgical tool motions. The disclosed disengagement-detection techniques are fully automatic. In other words, the UIDs and the surgical tools can become disengaged naturally by simply having the user putting the UIDs back to their docking positions without having to remember to take any additional action, while the docking motions of the UIDs are used by the trained classifier to automatically disengage the UIDs from the controlling the surgical tools.

Figure 1:
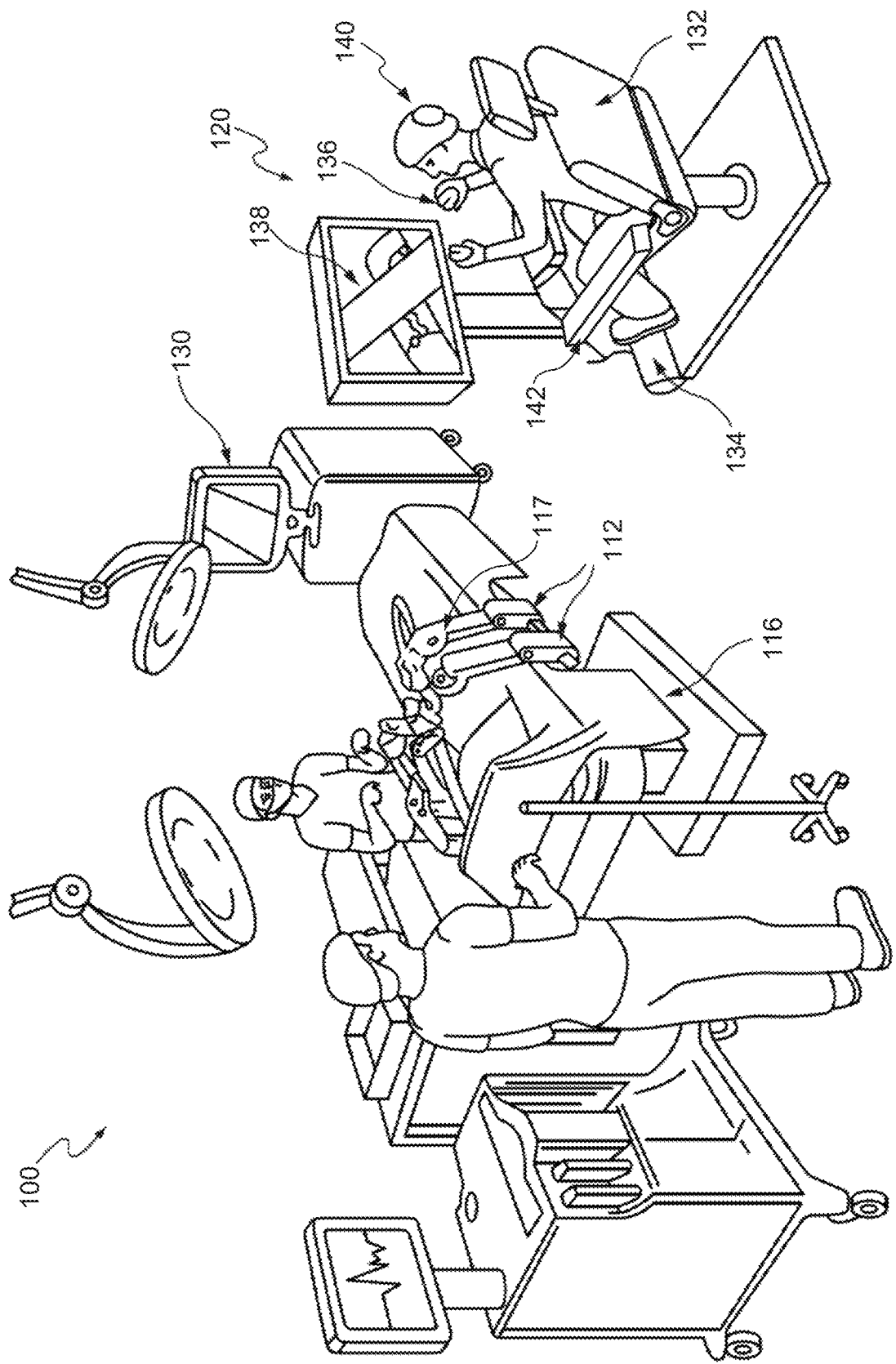
FIG. 1 shows a diagram illustrating an exemplary operating room environment with a robotic surgical system for implementing the disclosed UID disengagement-detection techniques in accordance with some embodiments described herein.

FIG. 1 shows a diagram illustrating an exemplary operating room environment with a robotic surgical system 100 for implementing the disclosed UID disengagement-detection techniques in accordance with some embodiments described herein. As shown in FIG. 1, robotic surgical system 100 comprises a user/surgeon console 120, a control tower 130, and one or more surgical robotic arms 112 located at a robotic surgical platform 116 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., teleoperation). User console 120 may be located in the same operating room as robotic surgical system 100, as shown in FIG. 1. In other environments, user console 120 may be located in an adjacent or nearby room, or teleoperated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms. Note that seat 132 can include a pair of armrests, such as a left armrest 142, which can be configured to receive and store UIDs 136 when they are not in use.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to achieve anesthesia. Initial access to the surgical site may be performed manually with robotic surgical system 100 in a stowed or withdrawn configuration to facilitate access to the surgical site. Once the access is achieved, initial positioning and/or preparation of the robotic system may be performed. During the procedure, a surgeon in the user console 120 may use the foot-operated controls 134 (e.g., one or more foot pedals) and/or UIDs 136 to manipulate various surgical tools/end effectors and/or imaging systems to perform the surgery. Manual assistance may also be provided at the procedure table by sterile-gowned personnel, who may perform tasks including, but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures including, but not limited to, robotic surgical system 100 cleaning and/or sterilization, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit them to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

In some implementations, user/operator 140 may hold and move a UID 136 in one hand to provide input commands to move a robotic arm actuator 117 in robotic surgical system 100. This UID 136 may be communicatively coupled to the rest of the robotic surgical system 100, e.g., via a console computer system (not shown) of user console 120. UID 136 may be ungrounded with respect to another component of robotic surgical system 100 while either tethered or untethered from user console 120. The term "ungrounded" is intended to refer to implementations where, for example, both UIDs are neither mechanically nor kinematically constrained with respect to user console 120. For example, user/operator 140 may hold a UID 136 in a hand and move freely to any possible position and orientation within space only limited by, for example, a tracking mechanism of the user console. Hence, the UID 136 can generate spatial state signals corresponding to movement of the UID, e.g., position and orientation of the handheld housing of the UID, and the spatial state signals may be input signals to control a motion of robotic arm actuator 117. Robotic surgical system 100 may use control signals derived from the spatial state signals, to control proportional motion of the actuator 117. In some embodiments, the console computer system of user console 120 receives the spatial state signals from the UID 136 and generates the corresponding control signals. Based on these control signals, which control how arm actuator 117 is energized to move a segment or link of a corresponding robotic arm 112, the movement of a corresponding surgical tool that is attached to the distal end of the robotic arm 112 may mimic the movement of the UID 136. Similarly, interaction between user/operator 140 and the UID 136 can generate for example, a grip control signal that causes a jaw of a grasper of the corresponding surgical tool to close and grip a tissue of a patient on top of robotic surgical platform 116.

Robotic surgical system 100 may include multiple UIDs 136, where respective control signals are generated for each UID 136 that control the actuators and the surgical tool (end effector) attached to a respective arm 112. For example, user/operator 140 may move a first UID 136 (e.g., the left UID) in one hand (e.g., the left hand) to control the motion of an arm actuator 117 that is in a left robotic arm 112, where the actuator responds by moving linkages, gears, etc., in the left robotic arm 112. Similarly, user/operator 140 may move a second UID 136 (e.g., the right UID) in the other hand (e.g., the right hand) to control the motion of another arm actuator 117 that is in a right robotic arm 112, which in turn moves other linkages, gears, etc., in the right robotic arm 112. Motions of a respective actuator 117 in a respective robotic arm 112 can be controlled by the spatial state signals generated from a respective UID 136. When user/operator 140 has finished manipulating the surgical tools with the UIDs 136, the user/operator may dock (i.e., store/rest) the UIDs 136 at designated docking areas/docking stations located at console 120. For example, user console 120 may include docking stations located at each of the left and right armrests of seat 132. To dock the left and right UIDs 136, the user may move the left UID 136 to the left docking station and the right UID 136 to the right docking station, and place each of the UIDs in their respective docking station holder, e.g., in form of a pocket.

Figure 2:
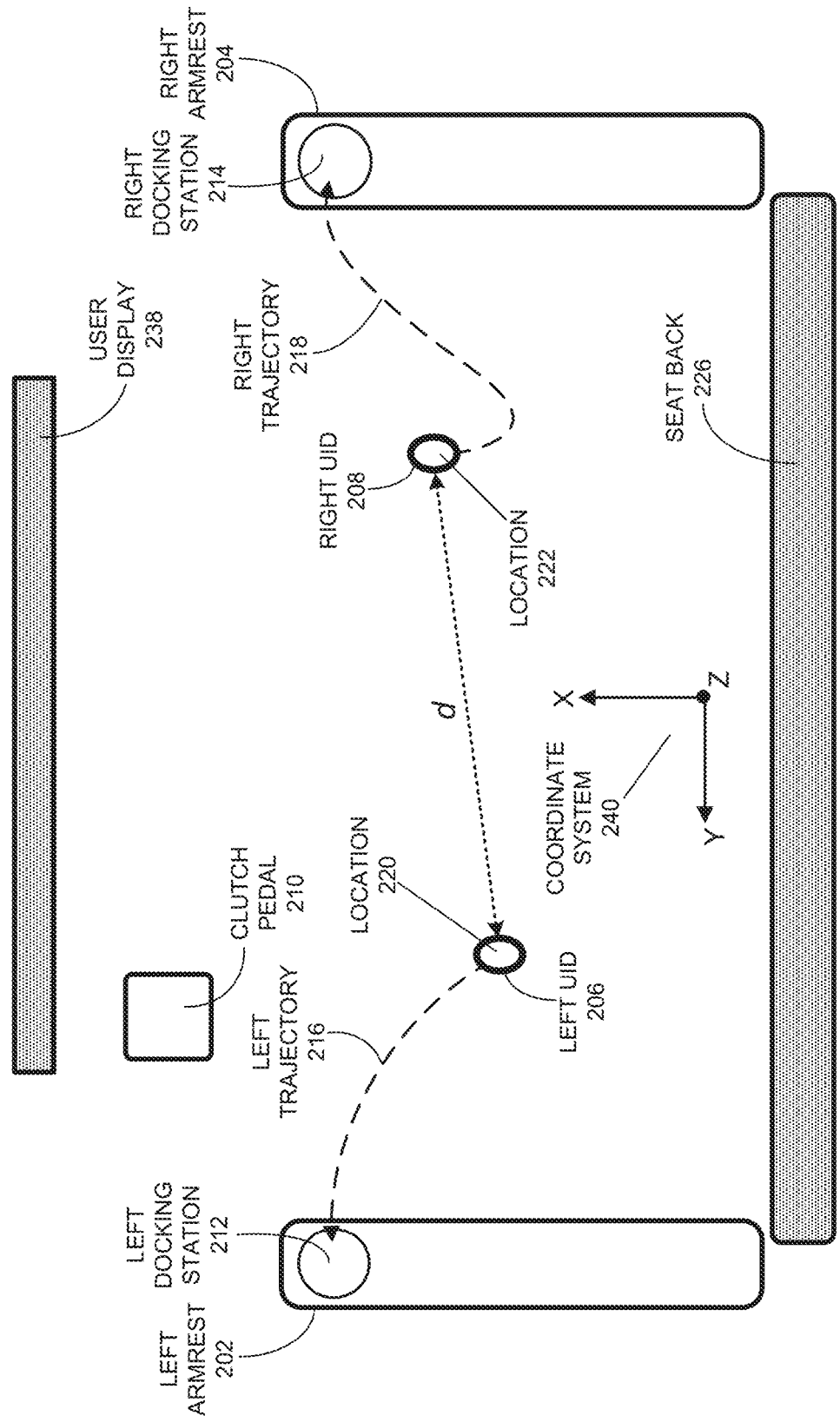
FIG. 2 illustrates an overhead view of an exemplary implementation of the user/surgeon console in the robotic surgical system of FIG. 1 in accordance with some embodiments described herein.

FIG. 2 illustrates an overhead view of an exemplary implementation 200 of user/surgeon console 120 in robotic surgical system 100 in accordance with some embodiments described herein. As can be seen in FIG. 2, exemplary surgeon console 200 includes at least a user display 238, a pair of armrests 202 (left) and 204 (right) of a user seat, a seat back 226 of the user seat, a pair of hand-held UIDs 206 and 208, and a foot clutch-pedal 210. Note that in exemplary surgeon console 200, the user seat is only partially shown. Further referring to FIG. 2, the left armrest 202 of the user seat further includes a left docking area/station 212, and the right armrest 204 of the user seat further includes a right docking area/station 214, respectively. In some embodiments, the left and right docking stations 212 and 214 are configured to serve as the designated parking/storing areas for the left and right UIDs 206 and 208, respectively, when UIDs 206 and 208 are not being used to control robotic tools. Exemplary surgeon console 200 also shows an exemplary Cartesian (x,y,z) coordinate system 240 for specifying the measured 3D positions of the left and right UIDs 206 and 208. This Cartesian coordinate system 240 will be discussed further below.

During telesurgery, after a surgeon at surgeon console 200 (not shown) has completed a teleoperation session or procedure by remotely manipulating robotic arms and/or surgical tools via the left and right UIDs 206 and 208, the surgeon can place the left and right UIDs 206 and 208 back to their respective docking stations 212 and 214, wherein the "docking" movements of the pairs of UIDs can follow exemplary trajectories 216 and 218, respectively. As described below, various disclosed UID disengagement-detection techniques can use sensors installed in the pair of armrests 202 or 204 to constantly detect whether a respective UID is in use, i.e., absent from the respective docking station, or not in use, i.e., present at the respective docking station. Although dock stations 212 and 214 are shown as circular areas in FIG. 2, other implementations of the docking stations 212 and 214 can have other shapes, such as rectangles, other than a circular shape.

In addition to simply receiving the UIDs and allowing the UIDs to be "parked" or otherwise stored at the docking stations, each of the docking stations 212 and 214 can also be integrated with an UID docking sensor (or simply "docking sensor," which is not explicitly shown in FIG. 2), which is configured to detect whether a respective UID is docked (i.e., returned to and being present at the docking station) or undocked (i.e., absent from/not present at the docking station). For example, the docking sensor in each of the armrest 202 or 204 can include a pressure sensor configured to detect the pressure changes in the docking station based on whether the respective UID 206 or 208 is docked or undocked. Alternatively, the docking sensor in each of the armrest 202 or 204 can include an inductive sensor configured to detect whether a respective UID 206 or 208 is docked/present or undocked/absent. In other embodiments, the docking sensor in each of the armrest 202 or 204 can include a touch sensor configured to detect whether a respective UID 206 or 208 in contact or not in contact with a surface of the respective docking station.

In various embodiments, each docking sensor in each of the armrest 202 or 204 is configured to generate binary time-series data to represent the two UID operation modes: i.e., a docked mode (or simply "docked") and an undocked mode (or simply "undocked"). For example, each docking sensor can output "LOW" or "0" values when the respective UID is undocked and absent from the respective docking station; and "HIGH" or "1" values when the respective UID is docked and present at the respective docking station. Note that when a UID is undocked, the UID may be involved in a teleoperation. However, a UID can also be undocked for other reasons not related to a teleoperation.

In the exemplary configuration of FIG. 2, the left and right UIDs 206 and 208 are both in the undocked mode and positioned in the three-dimensional (3D) space on the left side and right side of the surgeon console 200, respectively. More specifically, in this undocked mode, left and right UIDs 206 and 208 are typically in the left and right hands of the surgeon manipulation robotic arms/tools, and can hence move freely in 3D space. As will be described further below, each of the UIDs 206 and 208 includes position and orientation sensors to constantly measure the real-time positions and orientations of a respective UID when the UID is in the undocked mode. Based on the real-time 3D position signals of the two UIDs 206 and 208, it is also possible to constantly determine a spatial distance "d" between the two UIDs, as well as a "To Docking Station" distance between each of the two UIDs 206 and 208 and its corresponding docking station 212 and 214.

Note that the exemplary user/surgeon console 200 also include a foot clutch pedal 210 (or "clutch pedal" 210 hereinafter). Clutch pedal 210 may be configured to engage the UIDs, i.e., to enable the UIDs to control the movements of the robotic arms and/or surgical tools; and to disengage the UIDs, i.e., to disable the UIDs from controlling the movements of the robotic arms and/or surgical tools. In some embodiments, the binary actions of either pressing in or releasing the clutch pedal 210 can be used to immediately start or stop the controls of the left and right UIDs (i.e., engaging/disengaging the UIDs) on the movements of the robotic arms and/or surgical tools. Moreover, the action of pressing in (also referred to as "clutching in") clutch pedal 210 can indicate the beginning of a new teleoperation period; whereas the action of releasing (also referred to as "clutching out") clutch pedal 210 can indicate the end of a current teleoperation period. In some embodiments, clutch pedal 210 includes a clutch mode sensor configured to generate binary signal to represent the two clutch pedal modes, e.g., outputting "LOW" or "0" when the clutch pedal is clutched-out/disengaged; and outputting "HIGH" or "1" when the clutch pedal is clutched-in/engaged.

Conventionally, following the disengagements of the UIDs by clutching out clutch pedal 210, the UIDs 206 and 208 are then moved from some random locations in the 3D space to their respective docking stations 212 and 214 to be docked. It is assumed that when the surgeon begins to move the UIDs 206 and 208 toward their respective docking stations, the UIDs have already been decoupled from the robotic arms and the surgical tools. Hence, the safety of each disengagement action requires a precise timing of the clutching-out action and precise coordination between the hand motions and foot motions of the surgeon. It can be appreciated that this clutch-based approach to disengage the UIDs requires the users to take additional disengagement trainings. However, even after taking proper trainings, improper disengagements can still occur from time to time in actual teleoperations. For example, the user can still clutch out with some delay, i.e., a short time after the docking motions of UIDs 206 and 208 have begun. In some worse cases, a user may simply forget to clutch out and directly return the UIDs from the 3D space to the docking stations. In the above scenarios, the intended motions of returning the UIDs to their respective docking stations can cause unintended motions of the surgical tools inside a patient, which can lead to serious injuries.

One objective of this patent disclosure is to provide a solution which allows the surgeon/user to naturally and safely return the UIDs back to the docking stations after actively using the UIDs during a teleoperation period without having to remember to take a particular action such as releasing the clutch pedal, while preventing any unintended motions of the surgical tools. Hence, a fully automatic UID disengagement-detection system and technique is proposed which can be used to replace the clutch-based UID disengagement approach. In various embodiments, the disclosed UID disengagement-detection system and technique employs a machine-learning model constructed and trained to automatically detect and recognize the very beginning of an intended motion of returning the UIDs from the 3D space to the docking stations following a teleoperation period. The disclosed UID disengagement-detection system and technique can also include mechanisms to automatically and instantly disengage the UIDs from controlling the surgical tools once the intended docking motion has been detected and confirmed.

In various embodiments, each time robotic surgical system 100 enters a teleoperation mode with the UIDs engaged, the disclosed UID disengagement-detection system and technique can be automatically activated. Once activated, the disclosed UID disengagement-detection system and technique can be configured to constantly monitor, collect and process real-time sensor data associated with the motions of the UIDs. In some embodiments, the disclosed UID disengagement-detection system includes a deep-learning-based disengagement-detection model (also referred to as "deep-learning disengagement detector" or "disengagement-detection model" hereinafter), such as a long short-term memory (LSTM) network-based classifier which is trained to distinguish between a teleoperation pattern in the real-time UID motion data and a disengagement/docking pattern in the real-time UID motion data. When the UIDs are determined to be in the teleoperation mode, no action will be triggered by the disclosed deep-learning disengagement detector. However, once the beginning of the disengagement/docking pattern is detected, the disclosed deep-learning disengagement detector is configured to immediately trigger the disengagement of the UIDs from controlling the robotic arms/surgical tools and stop further movements of the robotic arms and surgical tools.

In various embodiments, to build a deep-learning disengagement detector which can make reliable and instant decisions for various UID motions, large amount of the training data from a wide range of relevant resources are collected, and the collected data are properly labeled. In some embodiments, the labeled training data for a collected time-series of UID motions clearly annotate and identify those data points and data patterns in the time-series corresponding to the teleoperation motions and those data points and data patterns in the time-series corresponding to the docking motions. Note that even though the disclosed UID disengagement detector is designed to eliminate the need for a clutch pedal, a clutch pedal can be useful and therefore used for the generation and labeling of time-series training data. This is because a well-trained user/surgeon can precisely time-synchronize a clutch-in action of the clutch pedal to the beginning of a new teleoperation period. Similarly, the same well-trained user/surgeon can precisely time-synchronize a clutch-out action of the clutch pedal to the end of a current teleoperation period and the beginning of a docking motion. Hence, with the assistance of the clutch pedal signals, a training-data labeler can more easily and accurately determine when the teleoperation period begins and ends, and when the docking motion starts. Note that because the disclosed disengagement-detection model is eventually used to make disengagement decisions on behalf of the human users, the training data should be labeled in such a manner to accurately reflect the actual human intentions, so that they can be used to teach the disengagement-detection model to make human-like decisions.

Figure 3:
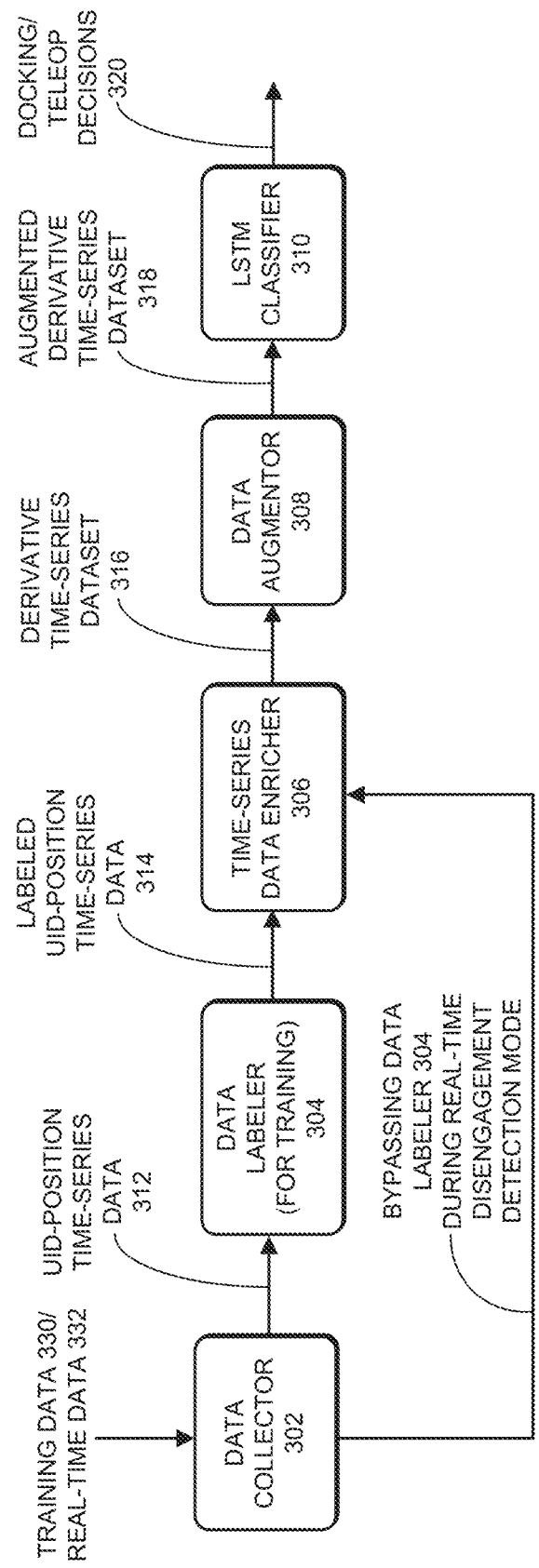
FIG. 3 shows a block diagram of an exemplary UID disengagement-detection system in accordance with some embodiments described herein.

FIG. 3 shows a block diagram of an exemplary UID disengagement-detection system 300 in accordance with some embodiments described herein. As shown in FIG. 3, disengagement-detection system 300 can include a data collector 302, a data labeler 304, a time-series data enricher 306, a data augmentor 308, and a long short-term memory (LSTM) network-based classifier 310 (or "LSTM classifier 310" hereinafter), which are coupled in the manner shown. Note that when data labeler 304 is included in disengagement-detection system 300, disengagement-detection system 300 is effectively in a model-training configuration for training LSTM classifier 310. However, if data labeler 304 is not used in disengagement-detection system 300 (e.g., as a pass-through module or being actively bypassed as shown in FIG. 3), and data collector 302 directly receives real-time UIDs position data during a given surgical procedure, disengagement-detection system 300 is in the real-time disengagement-detection configuration.

In some embodiments, data collector 302 interfaces various sensors within robotic surgical system 100 to read or otherwise collect artificially-generated training data 330, including UID motion data during training-data collection sessions exclusively for training-data collection purposes. In other embodiments, data collector 302 interfaces various sensors within robotic surgical system 100 to read or otherwise collect real-time sensor data 332 including UID motion data during actual surgical procedures. To collect UID motion data (also referred to as "UID motion signals"), data collector 302 can interface with the electromagnetic sensors within the left and right UIDs 206 and 208, respectively, and collect real-time positions and orientations of each of the left and right UIDs 206 and 208 manipulated by a user in the form of time-series. More specifically, the collected real-time UID motion data for each of the two UIDs 206 and 208 can include three time-series data of 3D UID positions (x,y,z); and four quaternions time-series data of UID orientations ($q_x$, $q_y$, $q_z$, $q_w$). In some embodiments, data collector 302 may interface with two eyeball-tracking sensors for collecting real-time eye-positions of the left eye and the right eye of the user manipulating the two UIDs. For example, the collected real-time eyeball-tracking sensors can include three time-series data of positions (x,y,z) of the left eyeball and three time-series data of positions (x,y,z) of the right eyeball.

In some embodiments, data collector 302 is coupled to the aforementioned UID docking sensor for each of the left and right UIDs 206 and 208. As described above, a UID docking sensor may be integrated with a respective armrest and configured to detect whether the respective UID is docked (i.e., returned to and present at the docking station) or undocked (i.e., not present at the docking station). In some embodiments, each UID docking sensor generates binary time-series signals to represent the two UID modes, e.g., outputting "LOW" or "0" when the respective UID is undocked from the respective docking station; and outputting "HIGH" or "1" when the respective UID is docked and present at the respective docking station. As will be discussed in more detail below, the collected docking sensor data can facilitate labeling the UID motion data collected during the same timeframe with higher accuracies and efficiencies. However, when the disclosed disengagement-detection system 300 is used in a real-time disengagement detection mode during a surgical procedure, these docking sensor data are generally not required.

In some embodiments, data collector 302 is also interfaced with the aforementioned clutch mode sensor which is configured to detect whether a clutch pedal is engaged (i.e., clutched in) or disengaged/released (i.e., clutched out). For example, this clutch mode sensor can generate binary data to represent the two clutch modes: i.e., "LOW" or "0" when the clutch pedal is disengaged/clutched-out; and "HIGH" or "1" when the clutch pedal is engaged/clutched-in. As mentioned above, a well-trained user/surgeon can precisely time-synchronize a clutch-in action to the beginning of a new telcoperation period; and precisely time-synchronize a clutch-out action to the end of a current telcoperation period and the beginning of a docking motion. As will be discussed in more detail below, the collected clutch mode sensor data can facilitate labeling the UID motion data collected during the same timeframe with significantly higher accuracies and efficiencies comparing to without such signals. However, when the disclosed disengagement-detection system 300 is used in a real-time disengagement detection mode during a surgical procedure, these docking sensor data are generally not required. In fact, even the clutch pedal itself, such as clutch pedal 210 can be eliminated from a given robotic surgical system when the disclosed disengagement-detection system is implemented in the given robotic surgical system.

In the disclosed disengagement-detection system 300, data collector 302 is coupled to data labeler 304, which is configured to receive UID-position time-series signal/data 312 and subsequently label the time-series signal/data 312 to identify those time periods in the time-series signal/data 312 which correspond to docking/disengagement motions of the UIDs, and separately identify those time periods in the time-series data 312 which correspond to motions other than the UID docking/disengagement motions, including all telcoperation actions. By accurately labeling the UID position signals consistent with the intended UID actions and user intentions, the properly labeled UID position signals can then be used to train LSTM classifier 310, so that the trained LSTM classifier 310 can automatically and accurately distinguish UID docking motions from non-docking UID motions including all teleoperation actions.

In some implementations, time-series data 312 includes three time-series of (x,y,z) positions for each of the left and right UIDs 206 and 208. In the discussion below, we assume that the 3D positions (x,y,z) of left UID 206 and the 3D positions (x,y,z) of right UID 208 are measured and obtained with respect to the same coordinate system. Prior to labeling time-series data 312, data labeler 304 may first convert each set of (x,y,z) positions of a given UID at a given time into a 3D position vector of the given UID, and subsequently compute a distance between the position vector of the given UID to the corresponding docking station of the given UID, thereby generating a single time-series of the UID distance to the corresponding docking station. Next, data labeler 304 is used to label the single time-series of the UID distance. In other embodiments, the (x,y,z) positions of the left and right UIDs can be directly labeled, and then the distance between the position vector (x,y,z) of the given UID to the corresponding docking station of the given UID is computed to generate a time-series of the UID distance. In this manner, the generated time-series of the UID distance will automatically include labels which are identical to the labels of the (x,y,z) positions.

Figure 4:
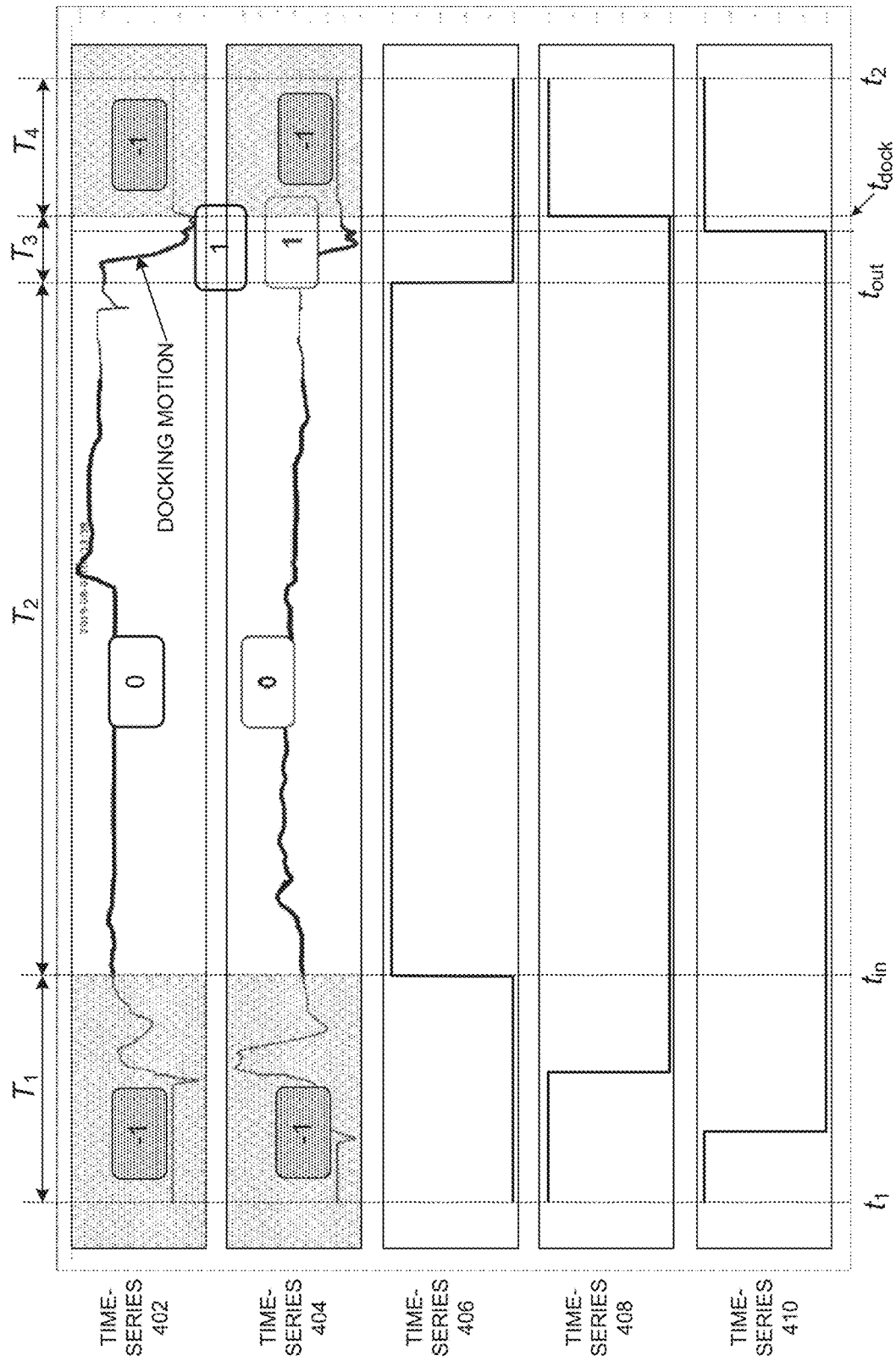
FIG. 4 illustrates an exemplary process of labeling the UID-position time-series data of both a left UID and a right UID to prepare training data for the long short-term memory (LSTM) network classifier in accordance with some embodiments described herein.

FIG. 4 illustrates an exemplary process of labeling the UID-position time-series data of both a left UID and a right UID to prepare training data for the LSTM classifier in accordance with some embodiments described herein. As can be seen, FIG. 4 shows five time series of robotic system data collected by data collector 302 during a time period 11 to 12, wherein all five time-series are time-synchronized to the same clock. Note that each of the time-series data is a slice of a much longer corresponding time-series signal collected during an actual training data generation process. More specifically, these time-series data are, from the top to bottom: (1) time-series 402 which is the position of the left UID relative to the left docking station, e.g., the left UID motion signal; (2) time-series 404 which is the position of the right UID relative to the right docking station, e.g., the left UID motion signal; (3) time-series 406 which is the clutch pedal signal; (4) time-series 408 which is the left UID docking sensor signal; and (5) time-series 410 which is the right UID docking sensor signal.

Note that time-series 402 and 404 also represent the motion of the corresponding UID. As can be seen in from these signals, initially from time $t_1$ the UIDs are docked at their respective docking stations, and as such, the position of a given UID relative to the respective docking station is at a minimum and stays unchanged. At some time after time $t_1$, the position value begins to increase indicating the given UID is being picked up and undocked from the docking station. Note that the left and right UIDs are undocked/picked up at slightly different times. After a short period of time, each UID position signal reaches a level of relative stability, e.g., around time $t_{in}$, indicating the corresponding UID motion also becomes more stable. This is when the two UIDs enter the teleoperation mode. Note that after a prolonged time period of teleoperation model including various surgical events, both time-series 402 and 404 signals begin to decrease sharply, e.g., around time $t_{out}$, indicating the teleoperation mode has ended and docking motions are in progress. Eventually, both time-series 402 and 404 signals return to the minimum values and stays unchanged, indicating the UIDs have been docked and again present at their respective docking stations.

In some embodiments, to label the UID motions represented by time-series 402 and 404, a human labeler can identify different time periods based on the above-described observations of the UID signal levels as one of three states/modes: (1) docked mode, i.e., don't-care mode corresponding to time periods $T_1$ and $T_4$; (2) teleoperation mode corresponding to time periods $T_2$; and (3) docking mode corresponding to time periods $T_3$. In the embodiment shown, both the left and the right UID motion signals are identified with the same set of time periods of $T_1$, $T_2$, $T_3$, and $T_4$, so that they do not need to be separately labeled. The human labeler can then assign a label "−1" to time periods $T_1$ and $T_4$ indicating these data do not matter; a label "0" to time period $T_2$ indicating the teleoperation mode; and a label "1" to time period $T_3$ indicating the docking action.

Note that the docking motion represented by time period $T_3$ is relatively short. In some embodiments, selecting the beginning of time period $T_3$ to be slightly before when the distance values begin to drop sharply allows for including the entire docking motion within time period $T_3$. Also note that such a labeling scheme aims at distinguishing teleoperation actions from docking actions. However, within the identified teleoperation mode "0", the disclosed disengagement-detection system 300 generally does not further distinguish different types of surgical events and motions, whether it is suturing, cautery, other types of tissue manipulations.

Note that the above-described manual labeling process can be time-consuming and susceptible to human errors. In some embodiments, it is possible to automate or semi-automate the UID motion data labeling with the help of the other available time-series. More specifically, the clutch pedal signal 406 shows that the clutch-in action occurs at time $t_{in}$, which can be used as the beginning of the teleoperation mode "0," i.e., the beginning of time period $T_2$. Similarly, the same clutch pedal signal 406 shows that the clutch-out action occurs at time $t_{out}$, which can be used as the end of the teleoperation mode "0," i.e., the end of time period $T_2$. Note that $t_{out}$ can also indicate the beginning of the docking mode "1," i.e., the beginning of time period $T_3$. As mentioned above, a well-trained user/surgeon can precisely synchronize/coordinate a clutch-in action to the beginning of a new telcoperation period; and also precisely synchronize/coordinate a clutch-out action to the end of a current teleoperation period and the beginning of a docking motion. Hence, when the time-series signals 402 and 404 are generated specifically for the purpose of preparing training data, the timestamps of $t_{in}$ and $t_{out}$ can be extracted from the clutch pedal actions to define the beginning and the end of teleoperation mode "0," which allows teleoperation mode label "0" for the UIDs to be automatically generated.

Furthermore, left UID docking signal 408 shows that the left UID is returned to the left docking station at time (dock, which can be used as the end of docking mode "1," i.e., the end of time period $T_3$ of time-series 402. Note that right UID docking signal 410 shows that the right UID is returned to the right docking station at a time slight earlier time than $t_{dock}$. However, the embodiment of FIG. 4 uses the same timestamp $t_{dock}$ as the end of docking mode "1" of time-series 404, which removes some complexity in the subsequent time-series data enriching process. On the other hand, if right UID docking signal 410 indicates that the right UID is returned to the right docking station at a time later than the moment of docking of left right UID, the moment of docking of the right UID can also be used as the end of docking modes "1" for both time-series 402 and 404, in place of timestamp $t_{dock}$. In either case, as long as the docking timestamps $t_{dock}$ can be extracted from UID docking signals 408 and 410, the aforementioned timestamp $t_{out}$ and the docking timestamps (dock can be used to define the beginning and the end of the docking mode "1," which allows docking mode label "1" for the two UIDs to be automatically generated.

Hence, when clutch pedal signal 406, the left UID docking signal 408, and the right UID docking signal 410 are all available, it becomes possible to make the UID motion data 402 and 404 labeling process fully automatic without human intervention or semi-automatic with only a minimum amount of human intervention.

Returning to FIG. 3 of disengagement-detection system 300, note that data labeler 304 is coupled to time-series data enricher 306 (or "data enricher 306"), which is configured to receive the labeled UID-position data 314, and derive/extract multiple derivative time-series (e.g., first order derivatives, second order derivatives, third order derivatives and so on) based on the UID-position data 314. Data enricher 306 subsequently outputs derivative time-series dataset 316 representing additional and enriched UID motion characteristics. Referring to FIG. 2, note that at the beginning of the docking motion, UIDs 206 and 208 can be located at some random locations 220 and 222 in the 3D space, and the user starts moving UIDs 206 and 208 from these random locations back to the docking stations following their respective trajectories 216 and 218. Note that the particular trajectories 216 and 218 that UIDs 206 and 208 follow during the docking motions also include a certain amount of randomness. If the labeled UID-position data 314 are directly used as the training data for LSTM classifier 310, the trained classifier will be biased based on the initial locations of the UIDs as well as the particular trajectories of the UID motions. For example, some users would always dock the UIDs starting from particular positions, where some other users would always dock the UIDs following particular patterns of trajectories. These personal preferences and habits, such as the specific starting locations of the UIDs would be learned by LSTM classifier 310 if they are not removed or otherwise mitigated in the training data, making the trained classifier 310 biased to these personal preferences.

In some embodiments, time-series data enricher 306 are configured to derive multiple sets of new time-series data based on the UID position data 314, wherein the new time-series data are not directly affected by the initial positions of the UIDs and the particular trajectories the UIDs take during docking motions. More specifically, the disclosed data enricher 306 generates multiple sets of new time-series data by computing multiple orders of derivatives of the UID position data 314 which eliminate the initial positions of the UIDs and eliminates or mitigate the particular trajectories the UIDs would take.

Figure 5:
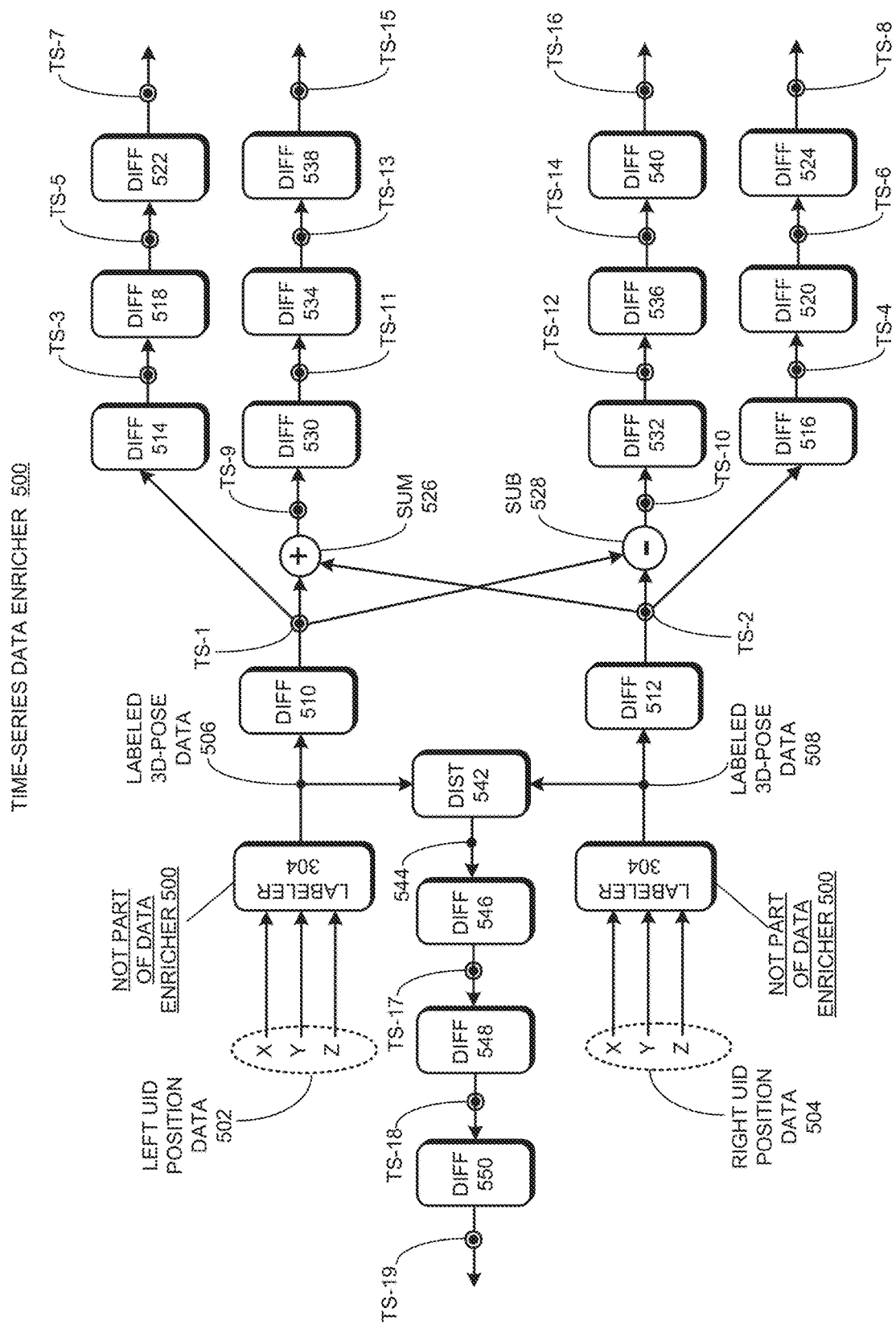
FIG. 5 illustrates an exemplary implementation of the time-series data enricher for extracting multiple sets of derivative time-series based on the UID position time-series data in accordance with some embodiments described herein.

FIG. 5 illustrates an exemplary implementation 500 of time-series data enricher 306 for extracting multiple sets of derivative time-series based on the UID position time-series data in accordance with some embodiments described herein. As can be seen in FIG. 5, the left-UID position data 502 and the right-UID position data 504 are received by data labeler 304 of disengagement-detection system 300, wherein each of the left and right-UID position data 502 and 504 further include three time-series of (x,y,z) positions. Data labeler 304 outputs labeled 3D-position data 506 of the left UID and labeled 3D-position data 508 for the right UID. Note that data labeler 304 is shown in FIG. 5 to facilitate visualizing its relationship to components of exemplary data enricher 500. However, data labeler 304 in FIG. 5 is not a part of exemplary data enricher 500.

As shown in FIG. 5, the first operators of data enricher 500 include a diff operator 510 (or "diff 510") and a diff operator 512 (or "diff 512"). Diff operator 510 receives labeled left-UID 3D-position data 506, computes the time-derivatives of the received left-UID position data, and outputs the first new time-series TS-1 representing the velocities of the left UID. Similarly, diff operator 512 receives labeled right-UID 3D-position data 508, computes the time-derivatives of the received right-UID position data, and outputs the second new time-series TS-2 representing the velocities of the right UID. Note that both of the new time-series TS-1 and TS-2 do not depend on the initial positions of the left and right UIDs. Also note that time-series TS-1 and TS-2 carry the same labels as the corresponding UID 3D-position data 506 and 508, and therefore do not need to be relabeled.

Data enricher 500 also includes a diff operator 514 (or "diff 514") and a diff operator 516 (or "diff 516"). Diff operator 514 receives velocity time-series TS-1, computes the time-derivatives of time-series TS-1, and outputs the third new time-series TS-3 representing the accelerations of the left UID. Similarly, diff operator 516 receives velocity time-series TS-2, computes the time-derivatives of time-series TS-2, and outputs the fourth new time-series TS-4 representing the accelerations of the right UID. Note that both of the new time-series TS-3 and TS-4 also do not depend on the initial positions of the left and right UIDs. Again, time-series TS-3 and TS-4 carry the same labels as the corresponding UID 3D-position data 506 and 508, and therefore do not need to be relabeled.

Data enricher 500 also includes a diff operator 518 (or "diff 518") and a diff operator 520 (or "diff 520"). Diff operator 518 receives acceleration time-series TS-3, computes the time-derivatives of time-series TS-3, and outputs the fifth new time-series TS-5 representing the jerks of the left UID. Similarly, diff operator 520 receives acceleration time-series TS-4, computes the time-derivatives of time-series TS-4, and outputs the sixth new time-series TS-6 representing the jerks of the right UID. Again, both of the new time-series TS-5 and TS-6 do not depend on the initial positions of the left and right UIDs and do not need to be relabeled.

Data enricher 500 additionally includes a diff operator 522 (or "diff 522") and a diff operator 524 (or "diff 524"). Diff operator 522 receives jerk time-series TS-5, computes the time-derivatives of time-series TS-5, and outputs the seventh new time-series TS-7 representing the snaps of the left UID. Similarly, diff operator 524 receives jerk time-series TS-6, computes the time-derivatives of time-series TS-6, and outputs the eighth new time-series TS-8 representing the snaps of the right UID. Again, both of the new time-series TS-7 and TS-8 do not depend on the initial positions of the left and right UIDs and do not need to be relabeled.

Data enricher 500 also includes a summation operator 526 (or "sum 526") which receives both velocity time-series TS-1 and velocity time-series TS-2, computes the sum of the two received time-series, and outputs the ninth new time-series TS-9 representing the combined velocities of the left UID and the right UID. Data enricher 500 further includes a subtraction operator 528 (or "sub 528") which receives both velocity time-series TS-1 and velocity time-series TS-2, computes the differences between the two received time-series, and outputs the tenth new time-series TS-10 representing the differences in velocities between the left UID and the right UID.

Data enricher 500 also includes a diff operator 530 (or "diff 530") which receives new time-series TS-9, computes the time-derivatives of time-series TS-9, and outputs the eleventh new time-series TS-11 representing the rate of changes of the combined velocities of the left UID and the right UID. Data enricher 500 further includes a diff operator 532 (or "diff 532") which receives new time-series TS-10, computes the time-derivatives of time-series TS-10, and outputs the twelfth new time-series TS-12 representing the rate of changes of the differences in velocities between the left UID and the right UID.

Data enricher 500 further includes a diff operator 534 (or "diff 534") which receives new time-series TS-11, computes the time-derivatives of time-series TS-11, and outputs the thirteenth new time-series TS-13 representing the rate of changes of time-series TS-11. Data enricher 500 further includes a diff operator 536 (or "diff 536") which receives new time-series TS-12, computes the time-derivatives of time-series TS-12, and outputs the fourteenth new time-series TS-14 representing the rate of changes of time-series TS-12.

Data enricher 500 further includes a diff operator 538 (or "diff 538") which receives new time-series TS-13, computes the time-derivatives of time-series TS-13, and outputs the fifteenth new time-series TS-15 representing the rate of changes of time-series TS-13. Data enricher 500 further includes a diff operator 540 (or "diff 540") which receives new time-series TS-14, computes the time-derivatives of time-series TS-14, and outputs the sixteenth new time-series TS-16 representing the rate of changes of time-series TS-14.

Data enricher 500 additionally includes distance operator 542 (or "dist 542") which receives labeled 3D-position data 506 and labeled 3D-position data 508, computes and outputs a distance time-series 544, which represents the spatial distance between the left UID and the right UID (for example, the distance "d" shown in FIG. 2 between UIDs 206 and 208). Note that distance time-series 544 carries the same labels as the UID position data 502 or 504, and therefore do not need to be relabeled. In some embodiments, because distance time-series 544 can be directly affected by the initial positions of the two UIDs and other biases in 3D-position data 506 and 508, time-series 544 itself is not outputted by data enricher 500 for the downstream data processing.

However, data enricher 500 further includes a diff operator 546 (or "diff 546") which receives distance time-series 544, computes the time-derivatives of time-series 544, and outputs the seventeenth new time-series TS-17 representing the rate of changes of distance time-series 544. Data enricher 500 also includes a diff operator 548 (or "diff 548") which receives new time-series TS-17, computes the time-derivatives of time-series TS-17, and outputs the eighteenth new time-series TS-18 representing the rate of changes of time-series TS-17. Finally, data enricher 500 includes a diff operator 550 (or "diff 550") which receives new time-series TS-18, computes the time-derivatives of time-series TS-18, and outputs the nineteenth new time-series TS-19 representing the rate of changes of time-series TS-18. Note that unlike distance time-series 544, new time-series TS-17, TS-18, and TS-19 do not depend on the initial positions of the left and right UIDs. Also note that time-series TS-17, TS-18, and TS-19 carry the same labels as the corresponding UID 3D-position data 506 and 508, and therefore do not need to be relabeled.

Overall from data enricher 500, 19 sets of new time-series are derived from the original 3D-position data 506 and 508 of the left and right UIDs. All these 19 sets of new time-series of data do not depend on the initial positions of the left and right UIDs, while each of these time-series adds an additional aspect of UID motion characteristics and an additional level of intelligence to facilitate training LSTM classifier 310 and generating faster and more accurate decisions by the trained LSTM classifier 310. As will be shown further below, enriching the time-series data used by the trained classifier 310 for disengagement detections allows for reducing the number of data points required to make each docking/teleoperation decision, thereby expediting the disengagement-detection speed.

Although the above-described data enriching technique generates 19 sets of derivative time-series based on computing one or more derivatives of the original UID 3D-position data 506 and 508, various embodiments of the UID disengagement-detection system 300 can use the full 19 sets of new time-series or a subset of the 19 new time-series dataset for the subsequent data processing. For example, one particular embodiment of data enricher 500 may only output a subset of the 19 new time-series dataset which is composed of the first order of derivatives (e.g., velocities) and the second order of derivatives (e.g., accelerations) of the original 3D-position data 506 and 508, i.e.: [TS-1, TS-2, TS-3, TS-4, TS-9, TS-10, TS-11, TS-12, TS-17 and TS-18]. Another exemplary embodiment of data enricher 500 may also output the same subset of the 19 new time-series dataset composed of the first order of derivatives and the second order of derivatives as in the previous example, but additionally output new time-series of the third order of derivatives, i.e., [TS-5, TS-6, TS-13, T-14, and TS-18].

Referring back to FIG. 3, note that disengagement-detection system 300 can also include data augmentor 308 following data enricher 306. In some embodiments, data augmentor 308 is configured to receive derivative time-series dataset 316, such as the above-described 19 sets of new time-series, swap the left UID data with the right UID data to effectively double the size of the received time-series dataset. As mentioned above, the 3D positions (x,y,z) of the left UID and the 3D positions (x,y,z) of the right UID are tracked and measured with respect to the same coordinate system.

Recall that FIG. 2 shows an exemplary (x,y,z) coordinate system 240 for specifying the measured 3D positions of the left and right UIDs. In this implementation, (x,y,z) coordinate system 240 for specifying the measured 3D positions of the left and right UIDs is set up such that: (1) the x-axis of the coordinate system is perpendicular to user display 238, with the positive axis pointing toward user display 238; (2) the y-axis of the coordinate system is parallel to the user display 238, with the positive axis pointing toward left armrest 202; (3) the z-axis of the coordinate system is perpendicular to the ground/floor, with the positive axis pointing upward; and (4) the origin of the coordinate system is substantially halfway between the left armrest 202 and right armrest 204. Note that in this exemplary coordinate system, the y-axis values of the left UID 206 are generally position; whereas y-axis values of the right UID 208 are generally negative.

Using the above exemplary coordinate system, in some embodiments, swapping the left UID data with the right UID data can be implemented by: (1) swapping the 3D positions (x,y,z) of the left UID and the 3D positions (x,y,z) of the right UID at each time-point in the time series; and (2) flipping/reversing the signs of the y-axis data of the swapped left UID data and the right UID data. For example, using this transformation, an original left UID data point (2, 4, 1) at a time-point to would create a new right UID data point (2, −4, 1) at time-point to; whereas an original right UID data point (3, −6, 2) at time-point to would create a new left UID data point (3, 6, 2) time-point to. In this manner, we created from the original pair of left and right UID positions [(2, 4, 1), (3, −6, 2)] a newly-created pair of left and right UID positions [(3, 6, 2), (2, −4, 1)]. When the above transformation is applied to all the UID data points in time-series dataset 316, the intended data swapping operation is complete. We collectively refer to the transformed/newly-created data points and the original time-series dataset 316 as the augmented derivative time-series dataset 318, which have the 2×size of the time-series dataset 316. Data augmentor 308 subsequently outputs augmented derivative time-series dataset 318 as an expanded dataset of derivative time-series dataset 316. Note that data augmentor 308 may be omitted in some implementations of the disclosed disengagement-detection system 300.

Finally in the disclosed disengagement-detection system 300 is LSTM classifier 310, which receives either augmented derivative time-series dataset 318 or derivative time-series dataset 316 directly from data enricher 306, processes the received time-series dataset 316 or 318, and generates real-time docking decisions and teleoperation decisions. Note that if disengagement-detection system 300 is in the training configuration, i.e., by actively including data labeler 304, then LSTM classifier 310 is trained with the labeled and enriched derivative time-series dataset 316 or the labeled and augmented derivative time-series dataset 318 to generate a trained LSTM classifier 310. Alternatively, if disengagement-detection system 300 is in the disengagement-detection configuration, i.e., without or bypassing data labeler 304, then LSTM classifier 310 receives unlabeled time-series dataset 316 or unlabeled time-series dataset 318 as inputs.

Figure 6:
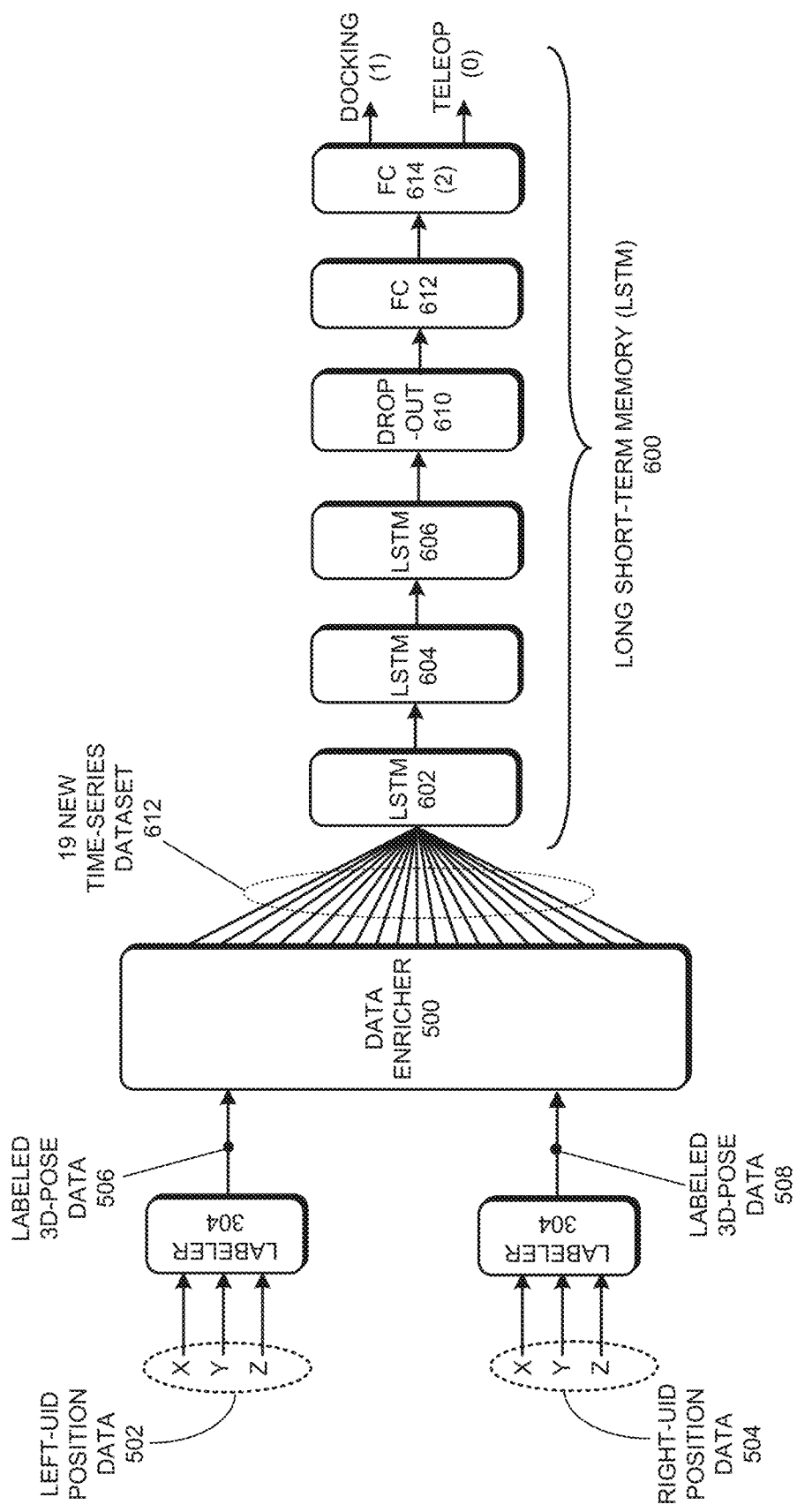
FIG. 6 illustrates an exemplary implementation of the LSTM classifier which receives the derivative time-series dataset from the disclosed data enricher in accordance with some embodiments described herein.

FIG. 6 illustrates an exemplary implementation 600 of LSTM classifier 310 which receives derivative time-series dataset from the above-described data enricher 500 in accordance with some embodiments described herein. From left to right, FIG. 6 first shows that the disclosed data labeler 304 receives the left-UID position data 502 and the right-UID position data 504, outputs labeled 3D-position data 506 and 508. FIG. 6 further shows that the disclosed data enricher 500 receives labeled 3D-position data 506 and 508 and outputs time-series dataset 602 including 19 sets of derivative time-series based on the above-described data enriching technique. Note that data labeler 304 and data enricher 500 are shown in FIG. 6 merely to facilitate visualizing the relationships of the various processing modules and various stages of the processed UID motion data to the exemplary LSTM classifier 600. However, data labeler 304 and data enricher 500 in FIG. 6 are not a part of LSTM classifier 600.

As can be seen in FIG. 6, the particular implementation of LSTM classifier 600 includes three stacked LSTM layers 602, 604, and 606, each of which includes hundreds of processing nodes (e.g., 100 nodes in each layer). Note that other embodiments of LSTM classifier 310 in the disclosed disengagement-detection system 300 can include fewer or greater number of LSTM layers without departing from the scope of the present technique. In LSTM classifier 600, the last LSTM layer 606 is coupled to a dropout layer 610 which performs dropout regularizations on the outputs of LSTM layer 606 to avoid overfitting of LSTM classifier 600. In some embodiments, dropout layer 610 has a dropout rate between 0.3-0.4. For example, in a particular embodiment, dropout layer 610 has a dropout rate of 0.3. In some implementations of LSTM classifier 310, additional dropout layers can be added between LSTM layers 602 and 604, and between LSTM layers 604 and 606. Dropout layer 610 is followed by two fully-connected (FC) layers FC 612 and FC 614. The first FC layer 612 receives the outputs from dropout layer 610 and maps them to a reduced set of decision nodes (e.g., 100 decision nodes). The second FC layer 614, i.e., the last layer in LSTM classifier 600 is a binary classification module which is configured to generate a binary decision at each decision time-point (e.g., according to a predetermined time internal) indicating whether the left and right UIDs are in a docking state/mode (1), or in a teleoperation state/mode (0). More specifically, FC 614 may include a decision threshold for converting a generated probability value into a final decision. For example, the decision threshold for outputting a docking decision (1) may be set to be at least 0.5 or higher.

Figure 7A:
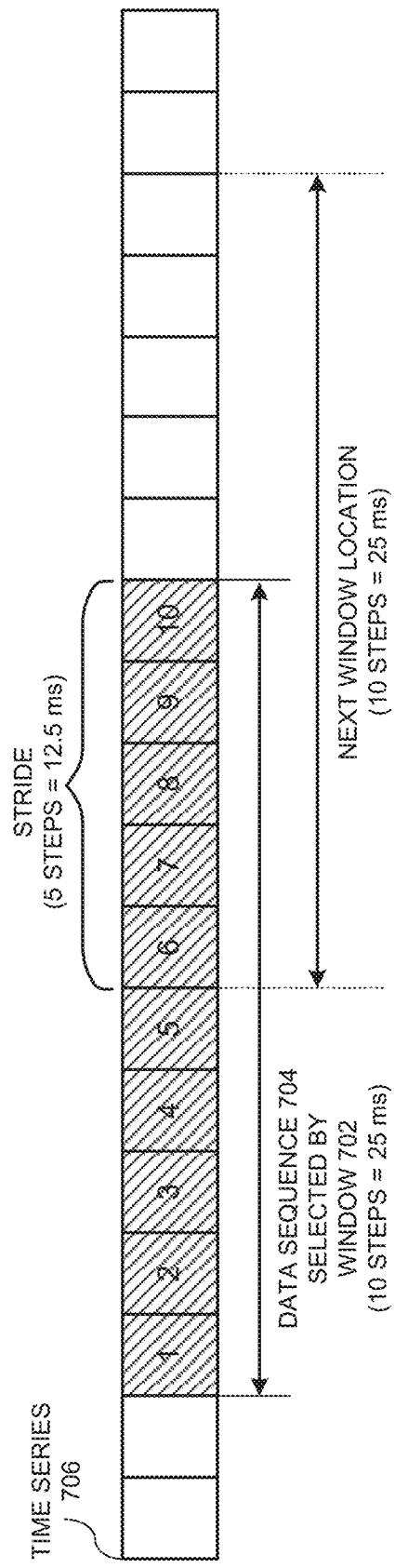
FIG. 7A shows using a slide window at a first window location to select a first data sequence of 10 data points from a given time series within the generated derivative time-series dataset in accordance with some embodiments described herein.

FIGS. 7A an 7B illustrates using a sliding windowing approach to process input UID position time-series data using LSTM classifier 310 in accordance with some embodiments described herein.

Specifically, FIG. 7A shows using a slide window 702 at a first window location to select a first data sequence 704 of 10 data points from a given time series 706 within the generated derivative time-series dataset 316 or 318 in accordance with some embodiments described herein. Note that the length of slide window 702 which contains 10 data points/steps from the time-series 706 corresponds to a time period of 25 ms based on a sensor readout frequency of 400 Hz (i.e., 2.5 ms/step). In some embodiments, the selected first data sequence 704 is read and fed into LSTM classifier 310, which processes the data to make one docking/teleoperation decision for the pair of UIDs.

Although the exemplary design of FIG. 7A uses a window size of 25 ms or 10 data points, the sliding window size may be generally determined based on system safety requirements which include a maximum time (e.g., 100 ms) allowed to stop the surgical tool movements to avoid unintended motions of the surgical tools. Note that a typical duration of UID docking actions can be around 1 sec. Because there can be other types of delays in the robotic surgical system 100 which would be added to the time of stopping, the design of the sliding window size should also take into account and therefore leave sufficient buffer for those delays. For example, if the maximum time allowed to stop the tool movement is 100 ms, the designed window size of 25 ms for each disengagement decision may be sufficiently fast. Note that other embodiments of slide window 702 in LSTM classifier 310 can use a longer or a shorter window size than 25 ms or 10 data points without departing from the scope of the present technique.

Generally speaking, LSTM classifier 310 and UID disengagement-detection system 300 should be designed to generate a disengagement decision immediately after an UID docking motion is detected (i.e., at the very beginning of the docking process, e.g., the beginning of timing window $T_3$ in FIG. 4), so that the surgical tool movements can be stopped at the beginning of the UID docking process. As mentioned above, the disclosed technique of enriching the time-series to be processed by LSTM classifier 310 with motion properties such as velocities, accelerations, jerks, snaps and other derivatives allows for significantly reducing the number of data points required to make each disengagement decision, thereby expediting the speed of data processing and disengagement detection as well as reducing the data size of the training dataset needed to fit the time-series training data to LSTM classifier 310.

Figure 7B:
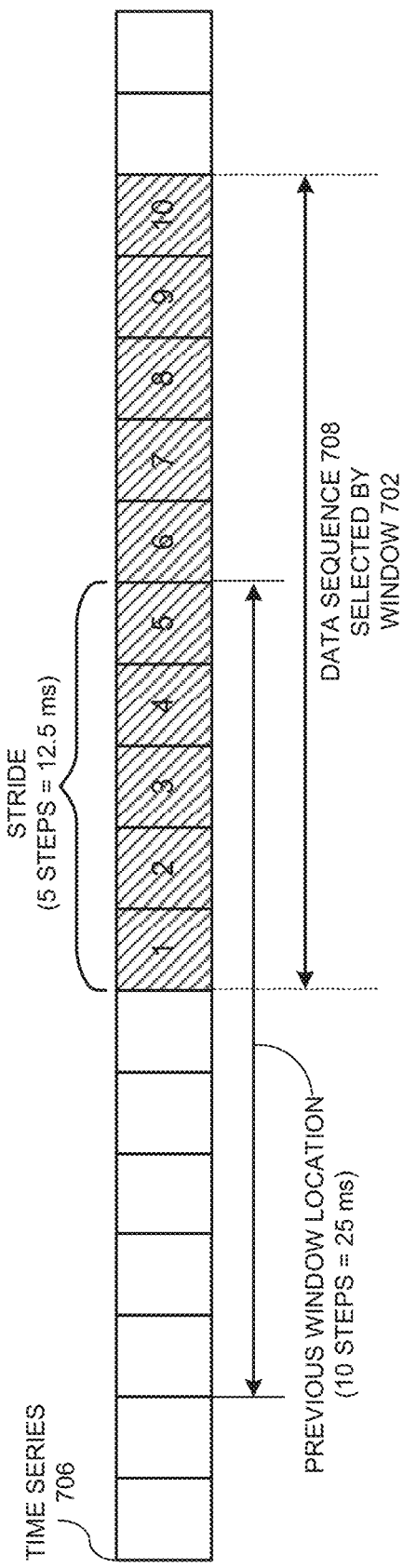
FIG. 7B shows using the same slide window at a second window location to select a second data sequence of 10 data points from the given time series in accordance with some embodiments described herein.

FIG. 7B shows using the same slide window 702 at a second window location to select a second data sequence 708 of 10 data points from time series 706 in accordance with some embodiments described herein. In some embodiments, second data sequence 708 is read and fed into LSTM classifier 310, which processes the data to make a new docking/teleoperation decision for the pair of UIDs. Note that in FIG. 7B, slide window 702 is moved forward by a stride of 5 data points or 12.5 ms to the second window location, such that the first window location and the second window location also have a partial overlap of 5 data points or 12.5 ms. Note that using a sliding window with a stride to allow a partial overlap between adjacent window locations allows the new window of data sequence to keep some memory of the previous window of data sequence. Moreover, with the partial overlap, the classifier decision interval is actually shorter than the window size. For example, in the exemplary design of FIG. 7B, the decision interval is about 50% of the window size or 12.5 ms. Note that other embodiments of the slide window 702 in LSTM classifier 310 can use a longer or shorter stride than 12.5 ms or 5 data points without departing from the scope of the present technique.

Figure 8:
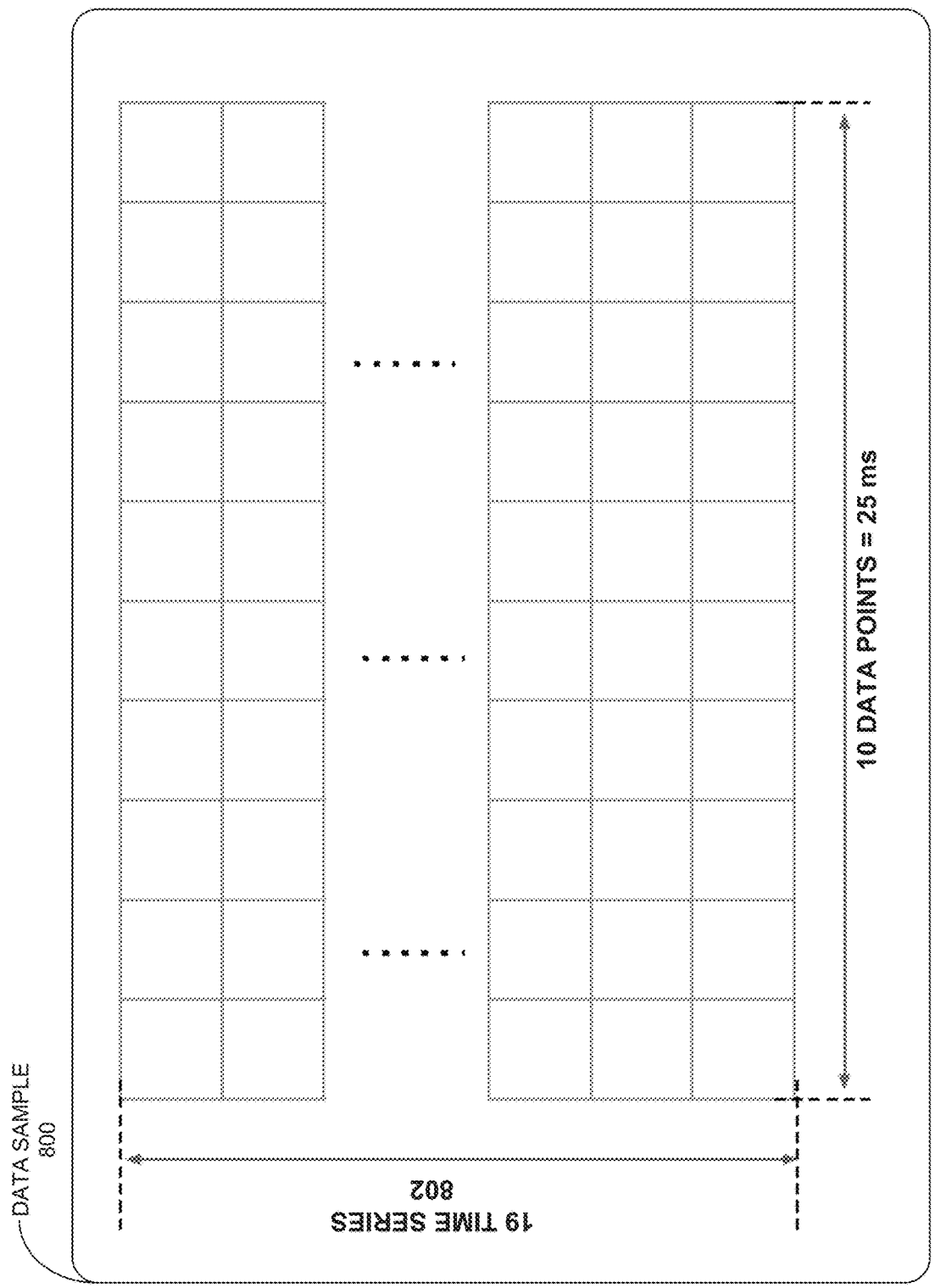
FIG. 8 shows the structure of a composite data sample generated based on 19 derivative time-series dataset and using a slide window to select 10 data points in the derivative time-series dataset in accordance with some embodiments described herein.

FIG. 8 shows the structure of a composite data sample 800 generated based on the above-described 19 derivative time-series dataset and the slide window technique to select 10 data points in the generated derivative time-series dataset in accordance with some embodiments described herein. As can be seen in FIG. 8, data sample 800 comprises a window of 10 data points of 25 ms across all 19 time series 802. Note that each single data sample 800 is then processed by LSTM classifier 310 to generate a single UID docking/teleoperation decision output.

In a practical implementation of disengagement-detection system 300, 5,259,140 windows of data samples having the above data structure were created based on a wide range of UID motion data collected from ~60 users over ~50 hours data generation and collection time. Of the 5,259,140 windows of data samples, 90% of the data samples were used as training data to train LSTM classifier 310 and 100% of the data samples were used in disengagement evaluations using the trained LSTM classifier 310. The evaluation results showed a docking/telcoperation decision accuracy of >99.9%.

Figure 9:
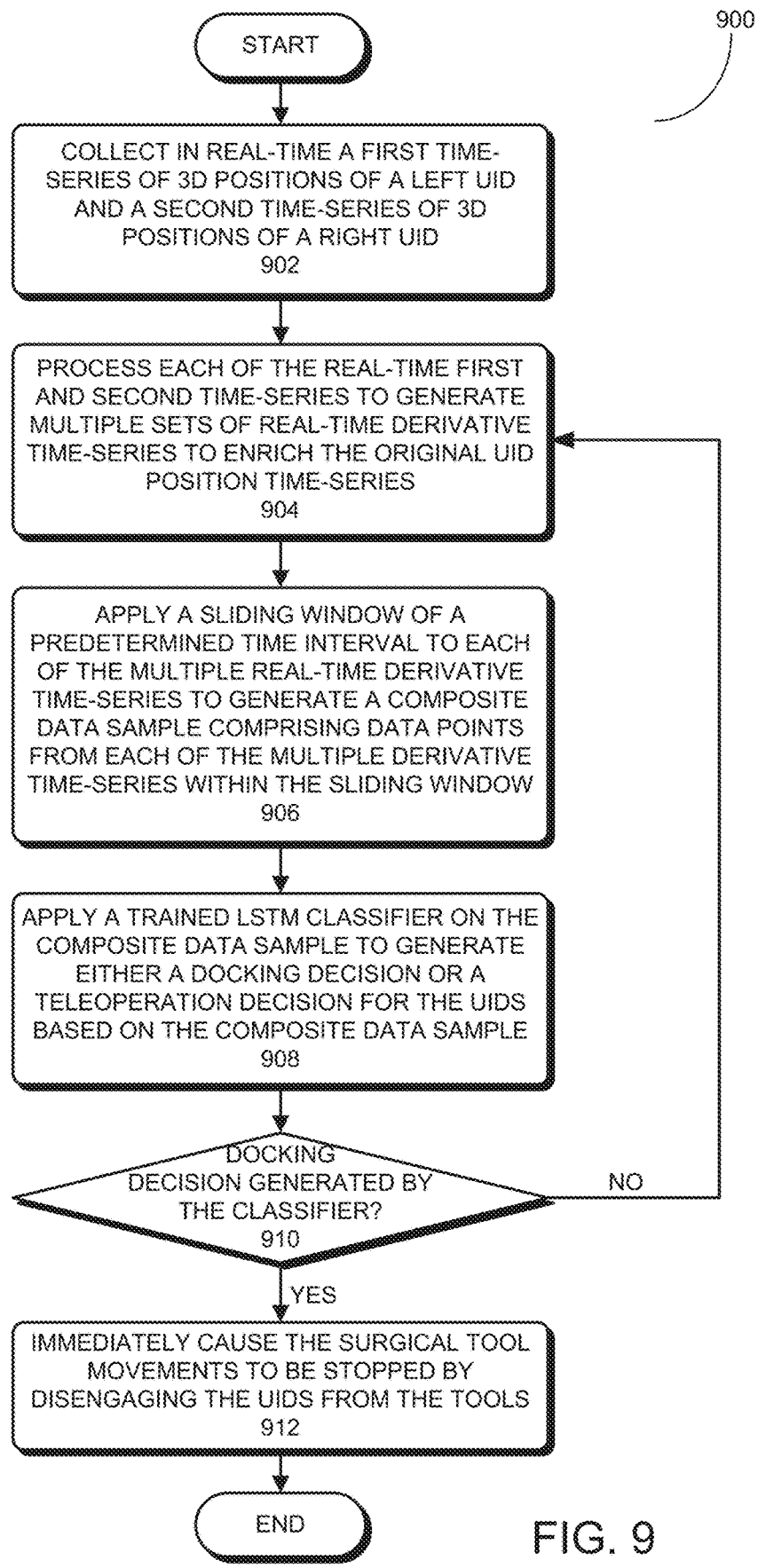
FIG. 9 presents a flowchart illustrating an exemplary process for performing deep-learning-based UID disengagement detections on robotic surgical system 100 during a surgical procedure in accordance with some embodiments described herein.

FIG. 9 presents a flowchart illustrating an exemplary process 900 for performing deep-learning-based UID disengagement detections on robotic surgical system 100 during a surgical procedure in accordance with some embodiments described herein. In one or more embodiments, one or more of the steps in FIG. 9 may be omitted, repeated, and/or performed in a different order. Accordingly, the specific arrangement of steps shown in FIG. 9 should not be construed as limiting the scope of the technique.

Process 900 may begin by collecting in real-time a first time-series of 3D positions of a left UID used to controlling the movement of a first surgical tool of robotic surgical system 100 and a second time-series of 3D positions of a right UID used to controlling the movement of a second surgical tool of robotic surgical system 100 (step 902). In some implementations, each of the first and second time-series of 3D positions includes three one dimensional (1D) time-series of (x,y,z) positions for each of the left and right UIDs. Next, process 900 processes each of the real-time first and second time-series to generate multiple sets of real-time derivative time-series of the first time-series and the second time-series to enrich the original UID position time-series (step 904). For example, the multiple sets of real-time derivative time-series can include some or all of the following 19 time series:

1. first order derivatives of the first time-series (TS1);
2. first order derivatives of the second time-series (TS2);
3. second order derivatives of the first time-series (TS3);
4. second order derivatives of the second time-series (TS4);
5. third order derivatives of the first time-series (TS5);
6. third order derivatives of the second time-series (TS6);
7. fourth order derivatives of the first time-series (TS7);
8. fourth order derivatives of the second time-series (TS8);
9. first order derivatives of the computed sum of TS1+TS2 (TS9);
10. first order derivatives of the computed difference of TS1−TS2 (TS10);
11. second order derivatives of the computed sum of TS1+TS2 (TS11);
12. second order derivatives of the computed difference of TS1−TS2 (TS11);
13. third order derivatives of the computed sum of TS1+TS2 (TS13);
14. third order derivatives of the computed difference of TS1−TS2 (TS14);
15. fourth order derivatives of the computed sum of TS1+TS2 (TS15);
16. fourth order derivatives of the computed difference of TS1−TS2 (TS16);
17. first order derivatives of distances between the first time-series and the second first time-series (TS17);
18. second order derivatives of time-series TS17 (TS18); and
19. third order derivatives of time-series TS18 (TS19).

Next, process 900 applies a sliding window of a predetermined time interval to each of the multiple real-time derivative time-series to generate a composite data sample comprising data points from each of the multiple derivative time-series within the sliding window (step 906). In some embodiments, the predetermined time interval was experimentally determined as the shortest time interval that could yield sufficient high docking and teleoperation detection accuracy. Subsequently, process 900 applies a trained LSTM classifier on the composite data sample to generate either a docking decision or a teleoperation decision for the left and right UIDs based on the composite data sample (step 908). Process 900 next determines if a docking decision is generated by the LSTM classifier on the composite data sample (step 910). If so, process 900 immediately causes the surgical tool movements to be stopped by disengaging the left and right UIDs from the first and second surgical tools, thereby preventing unintended surgical tool motions (step 912). Otherwise, process 900 returns to step 904 to continue monitoring the real-time left and right UIDs movements.

In some embodiments, robotic surgical system 100 implementing the disclosed UID disengagement-detection system 300 is configured to disengage the left and right UIDs from the surgical tools they are controlling anytime a docking decision (1) is generated by the LSTM classifier based on the real-time UID motion signals. However, this approach may be subject to certain false alarms. In other embodiments, robotic surgical system 100 implementing the disclosed UID disengagement-detection system 300 disengages the left and right UIDs from the surgical tools they are controlling only when a minimum number (e.g., 3-5) of consecutive docking decisions (1) have been generated by the LSTM classifier based on the real-time UID motion signals.

Figure 10:
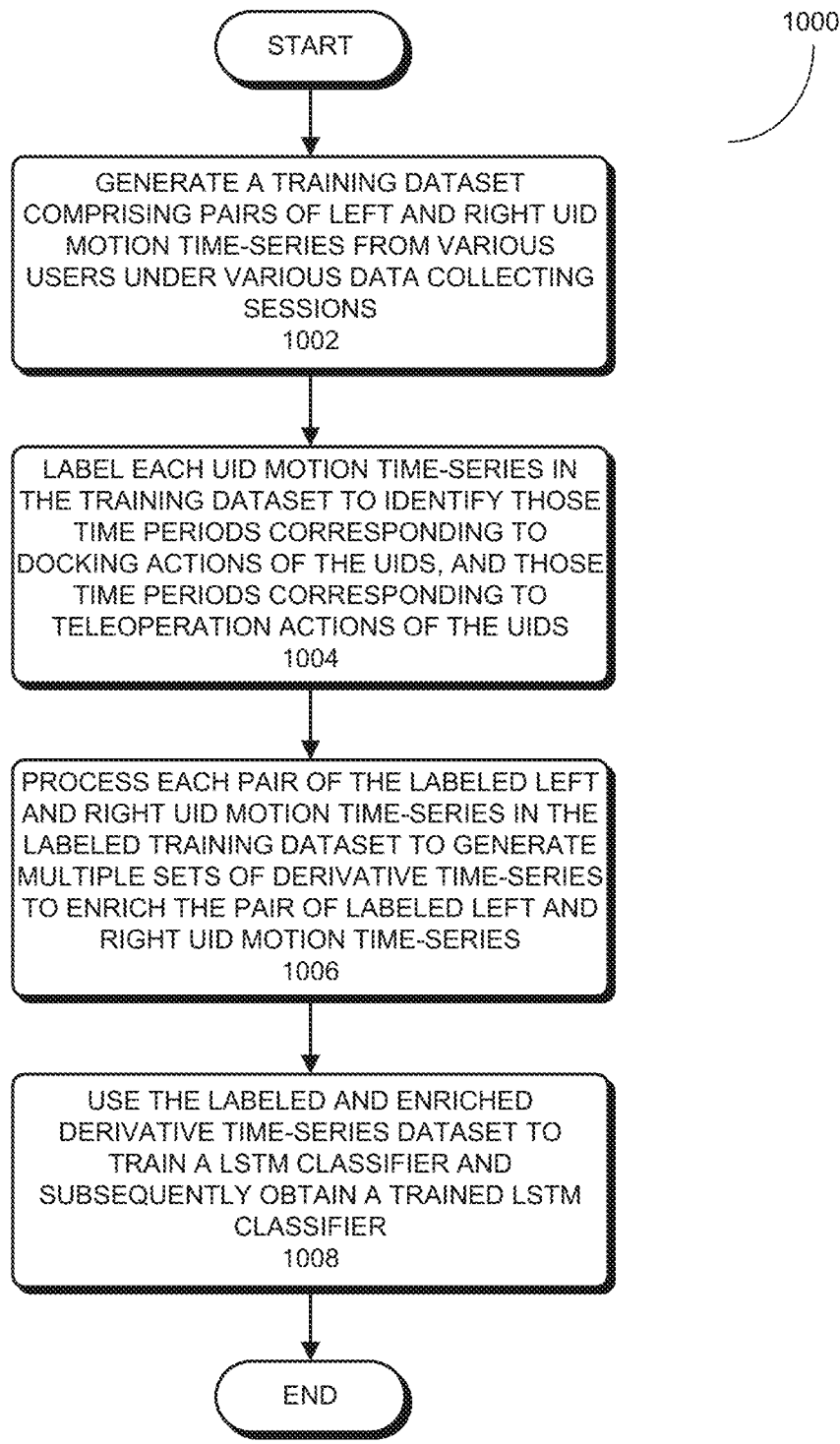
FIG. 10 presents a flowchart illustrating an exemplary process for training the LSTM classifier used in process 900 for performing the disclosed disengagement detections in accordance with some embodiments described herein.

FIG. 10 presents a flowchart illustrating an exemplary process 1000 for training the LSTM classifier used in process 900 for performing the disclosed disengagement detections in accordance with some embodiments described herein. In one or more embodiments, one or more of the steps in FIG. 10 may be omitted, repeated, and/or performed in a different order. Accordingly, the specific arrangement of steps shown in FIG. 10 should not be construed as limiting the scope of the technique.

Process 1000 may begin by generating a training dataset comprising pairs of left and right UID motion time-series from various users under various data collecting sessions (step 1002). For example, process 1000 can collect artificially-generated training data of left and right UID motion time-series during training-data collection sessions exclusively for training-data collection purposes. Process 1000 can also collect real-time training data of left and right UID motion time-series during actual surgical procedures. In some embodiments, each of the collected time-series is further composed of three 1D time-series of (x,y,z) positions of a corresponding UID. Next, process 1000 labels each UID motion time-series in the training dataset to identify those time periods corresponding to docking actions of the UIDs, and those time periods corresponding to teleoperation actions of the UIDs (step 1004). As mentioned above, by extracting time information from accompanying clutch pedal signals, and the associated left and right UID docking signals, labeling various UID motion time-series in the training dataset can be a fully-automatic process.

Next, process 1000 processes each pair of the labeled left and right UID motion time-series in the labeled training dataset to generate multiple sets of derivative time-series to enrich the original pair of labeled left and right UID motion time-series (step 1006). For example, process 1000 can use the time-series data enriching technique described in conjunction with FIG. 5 to generate 19 sets of derivative time-series for each pair of the labeled left and right UID motion time-series. As described-above, the 19 sets of derivative time-series generated based on the pair of the labeled left and right UID motion time-series do not depend on the initial positions of the left and right UIDs and do not need to be relabeled. In some embodiments, process 1000 can optionally augment the labeled and enriched training dataset to effectively expand the training dataset. For example, process 1000 can simply swap the left UID data with the right UID data to effectively double the size of the labeled and enriched training dataset. Process 1000 subsequently uses the labeled and enriched derivative time-series dataset to train a LSTM classifier and subsequently generates a trained LSTM classifier (step 1008). Note that the trained LSTM classifier can then be used to generate real-time docking decisions and teleoperation decisions by receiving and processing real-time UID motion data during a surgical procedure.

Figure 11:
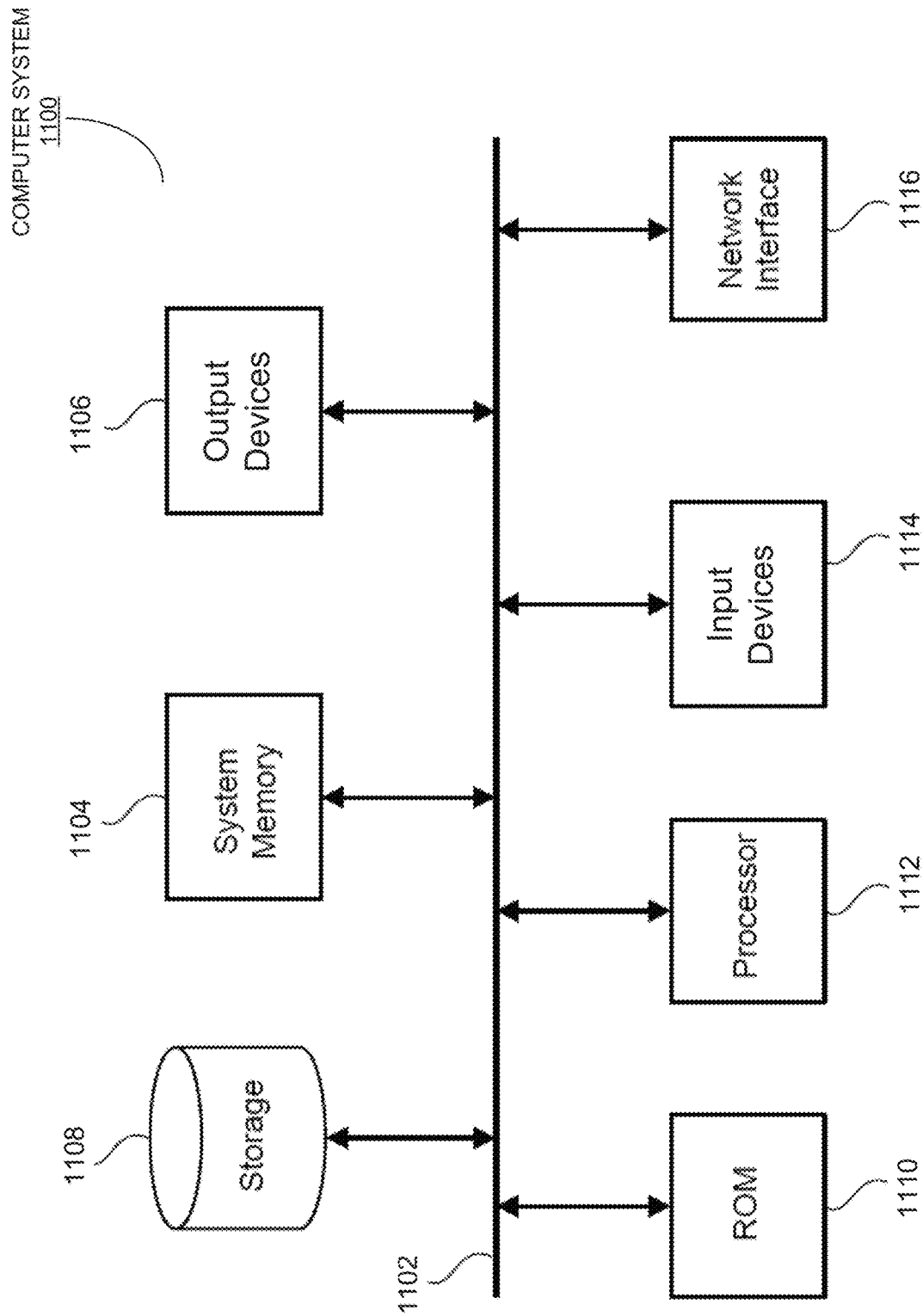
FIG. 11 conceptually illustrates a computer system with which some embodiments of the subject technology can be implemented.

FIG. 11 conceptually illustrates a computer system with which some embodiments of the subject technology can be implemented. Computer system 1100 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 1100 includes a bus 1102, processing unit(s) 1112, a system memory 1104, a read-only memory (ROM) 1110, a permanent storage device 1108, an input device interface 1114, an output device interface 1106, and a network interface 1116. In some embodiments, computer system 1100 is a part of a robotic surgical system.

Bus 1102 collectively represents all system, peripheral, and chipset buses that communicatively connect the numerous internal devices of computer system 1100. For instance, bus 1102 communicatively connects processing unit(s) 1112 with ROM 1110, system memory 1104, and permanent storage device 1108.

From these various memory units, processing unit(s) 1112 retrieves instructions to execute and data to process in order to execute various processes described in this patent disclosure, including the above-described techniques for performing real-time UID disengagement detections in the robotic surgical system described in conjunction with FIGS. 2-10. The processing unit(s) 1112 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 1112 can be a single processor or a multi-core processor in different implementations.

ROM 1110 stores static data and instructions that are needed by processing unit(s) 1112 and other modules of the computer system. Permanent storage device 1108, on the other hand, is a read-and-write memory device. This device is a non-volatile memory unit that stores instructions and data even when computer system 1100 is off. Some implementations of the subject disclosure use a mass-storage device (such as a magnetic or optical disk and its corresponding disk drive) as permanent storage device 1108.

Other implementations use a removable storage device (such as a floppy disk, flash drive, and its corresponding disk drive) as permanent storage device 1108. Like permanent storage device 1108, system memory 1104 is a read-and-write memory device. However, unlike storage device 1108, system memory 1104 is a volatile read-and-write memory, such as a random access memory. System memory 1104 stores some of the instructions and data that the processor needs at runtime. In some implementations, various processes described in this patent disclosure, including the above-described techniques for performing real-time UID disengagement detections in the robotic surgical system described in conjunction with FIGS. 2-10, are stored in system memory 1104, permanent storage device 1108, and/or ROM 1110. From these various memory units, processing unit(s) 1112 retrieves instructions to execute and data to process in order to execute the processes of some implementations.

Bus 1102 also connects to input and output device interfaces 1114 and 1106. Input device interface 1114 enables the user to communicate information and select commands for the computer system. Input devices used with input device interface 1114 include, for example, alphanumeric keyboards and pointing devices (also called "cursor control devices"). Output device interface 1106 enables, for example, the display of images generated by the computer system 1100. Output devices used with output device interface 1106 include, for example, printers and display devices, such as cathode ray tubes (CRT) or liquid crystal displays (LCD). Some implementations include devices such as a touchscreen that functions as both input and output devices.

Finally, as shown in FIG. 11, bus 1102 also couples computer system 1100 to a network (not shown) through a network interface 1116. In this manner, the computer can be a part of a network of computers (such as a local area network ("LAN"), a wide area network ("WAN"), an intranet, or a network of networks, such as the Internet. Any or all components of computer system 1100 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for detecting an intention to disengage from a surgical tool in a robotic surgical system, the method comprising:
   receiving a plurality of time-series which include i) a first time-series of positions of a first user input device, UID, controlling a movement of a first surgical tool and ii) a second time-series of positions of a second UID controlling a movement of a second surgical tool;
   applying the plurality of time-series to a neural network classifier, wherein the neural network classifier is trained to detect disengagement and teleoperation motions of the first UID and the second UID and generate either a disengagement decision or a teleoperation decision; and
   in response to receiving the disengagement decision from the neural network classifier, disengaging the first UID and the second UID from controlling the first and second surgical tools.

2. The computer-implemented method of claim 1, wherein each of the first and second time-series of positions of the first UID and the second UID is a time-series of three-dimensional, 3D, positions of a respective UID.

3. The computer-implemented method of claim 2, further comprising:
   computing a derivative of the first time-series to generate a first derivative time-series of the first UID representative of a velocity of the first UID;
   computing the derivative of the second time-series to generate a second derivative time-series of the second UID representative of a velocity of the second UID; and
   applying the first derivative time-series and the second derivative time-series as input to the neural network classifier.

4. The computer-implemented method of claim 3, further comprising:
   computing the derivative of the first derivative time-series to generate a third derivative time-series of the first UID representative of an acceleration of the first UID; and
   computing the derivative of the second derivative time-series to generate a fourth derivative time-series of the second UID representative of an acceleration of the second UID, and wherein the neural network classifier is configured to receive as input the third derivative time-series and the fourth derivative time-series.

5. The computer-implemented method of claim 4, further comprising:
   computing the derivative of the third derivative time-series to generate a fifth derivative time-series of the first UID representative of a jerk of the first UID; and
   computing the derivative of the fourth derivative time-series to generate a sixth derivative time-series of the second UID representative of a jerk of the second UID, and wherein the neural network classifier is configured to receive as input the fifth derivative time-series and the sixth derivative time-series.

6. The computer-implemented method of claim 5, further comprising:
   computing the derivative of the fifth derivative time-series to generate a seventh derivative time-series of the first UID representative of a snap of the first UID; and
   computing the derivative of the sixth derivative time-series to generate an eighth derivative time-series of the second UID representative of a snap of the second UID, wherein the neural network classifier is configured to receive as input the seventh derivative time-series and the eighth derivative time-series.

7. The computer-implemented method of claim 3, further comprising:
   computing a ninth time-series by summing the first derivative time-series and the second derivative time-series representative of combined velocities of the first UID and the second UID;
   computing a tenth time-series by performing a subtraction between the first derivative time-series and the second derivative time-series representative of differences in velocities between the first UID and the second UID;
   computing the derivative of the ninth time-series to generate an eleventh derivative time-series representative of a rate of change of the combined velocities; and
   computing the derivative of the tenth time-series to generate a twelfth derivative time-series representative of a rate of change of the differences in velocities, wherein the neural network classifier is configured to receive as input the eleventh derivative time-series and the twelfth derivative time-series.

8. The computer-implemented method of claim 3, further comprising:
   generating a distance time-series by computing a set of distance values between each 3D position in the first derivative time-series and a corresponding 3D position in the second derivative time-series representative of distances between the first UID and the second UID;
   computing the derivative of the distance time-series to generate a fifteenth derivative time-series representative of a rate of change of the distances between the first UID and the second UID;

computing the derivative of the fifteenth derivative time-series to generate a sixteenth derivative time-series representative of a rate of change of the fifteenth derivative time-series; and computing the derivative of the sixteenth derivative time-series to generate a seventeenth derivative time-series representative of a rate of change of the sixteenth derivative time-series.

9. The computer-implemented method of claim 3, wherein applying the first derivative time-series and the second derivative time-series as input to the neural network classifier includes:

applying a sliding window of a predetermined window size to each of the first derivative time-series to generate a composite data sample comprising a set of data points from each of the first derivative time-series within the sliding window; and applying the neural network classifier on the composite data sample to generate either the disengagement decision or the teleoperation decision based on the composite data sample.

10. The computer-implemented method of claim 1, wherein prior to applying the plurality of time-series to the neural network classifier, the method further comprises training the neural network classifier by:

receiving a first plurality of time-series of positions of a left UID and a second plurality of time-series of positions of a right UID;

for each time-series in the first plurality of time-series and a corresponding time-series in the second plurality of time-series:

annotating the time-series to identify each teleoperation event in the time-series and each UID docking event in the time-series; and processing the annotated time-series to generate a plurality of derivative time-series of the first plurality of time-series and the second plurality of time-series; and using the plurality of derivate time-series of the first plurality of time-series and the second plurality of time-series as training data to train the neural network classifier.

11. The computer-implemented method of claim 10, wherein annotating the time-series to identify each teleoperation event in the time-series includes:

identifying a first timestamp corresponding to the beginning of a teleoperation event and a second timestamp corresponding to the end of the teleoperation event; and labeling each data point between the first timestamp and the second timestamp with a first value indicative of a teleoperation mode.

12. The computer-implemented method of claim 11, wherein annotating the time-series to identify each UID docking event in the time-series includes:

identifying a third timestamp corresponding to the beginning of a UID docked mode; and labeling each data point between the second timestamp and the third timestamp with a second value indicative of a disengagement mode, wherein the disengagement mode terminates when the UID docked mode begins.

13. The computer-implemented method of claim 1, wherein the disengagement motions include docking motions of returning the first and second UIDs to respective docking stations.

14. The computer-implemented method of claim 1, wherein the neural network classifier includes a plurality of LSTM layers followed by a dropout layer with a dropout rate between 0.3-0.4, e.g., a dropout rate=0.3.

15. An apparatus for detecting a disengagement intention from a surgical tool in a robotic surgical system, the apparatus comprising:

one or more processors; and a memory coupled to the one or more processors, the memory storing instructions that, when executed by the one or more processors, cause the apparatus to:

receive a first time-series of positions of a first user input device (UID) controlling a movement of a first surgical tool and a second time-series of positions of a second user input device (UID) controlling a movement of a second surgical tool;

process the first time-series and the second time-series to generate a plurality of derivative time-series of the first time-series and the second time-series;

apply a neural network classifier on the plurality of derivative time-series, wherein the neural network classifier is trained to detect disengagement and teleoperation motions of the first and second UIDs and generate either a disengagement decision or a teleoperation decision; and in response to receiving the disengagement decision from the neural network classifier, disengaging the first and second UIDs from controlling the first and second surgical tools.

16. The apparatus of claim 15, wherein the memory further stores instructions that, when executed by the one or more processors, cause the apparatus to generate the plurality of derivative time-series by:

computing a derivative of the first time-series to generate a first derivative time-series of the first UID representative of a velocity of the first UID; and computing the derivative of the second time-series to generate a second derivative time-series of the second UID representative of a velocity of the second UID.

17. The apparatus of claim 16, wherein the memory further stores instructions that, when executed by the one or more processors, cause the apparatus to apply the neural network classifier to the plurality of derivative time-series by:

applying a sliding window of a predetermined window size to each of the first derivative time-series and the second derivative time-series to generate a composite data sample comprising a set of data points within the sliding window; and applying the neural network classifier on the composite data sample to generate either a disengagement decision or a teleoperation decision based on the composite data sample.

18. The apparatus of claim 15, wherein the memory further stores instructions that, when executed by the one or more processors, cause the apparatus to train the neural network classifier by:

receiving a first plurality of time-series of positions of a left UID and a second plurality of time-series of positions of a right UID;

for each time-series in the first plurality of time-series and a corresponding time-series in the second plurality of time-series:

annotating the time-series to identify each teleoperation event in the time-series and each UID disengagement event in the time-series; and processing the annotated time-series to generate a plurality of derivative time-series of the first time-series and the second time-series; and using the annotated and processed derivatives of first plurality of time-series and the second plurality of time-series as training data to train the neural network classifier.

19. A robotic surgical system, comprising:
a first and a second surgical tools;
a first and a second user interface device (UID) for controlling movements of the first and the second surgical tools, respectively; and
a computer coupled to the first and the second surgical tools and the first and the second UIDs and configured to perform real-time UID disengagement detections by:
   receiving a first time-series of positions of the first UID and a second time-series of positions of the second UID;
   processing the first time-series and the second time-series to generate a plurality of derivative time-series of the first time-series and the second time-series;
   applying a neural network classifier on the plurality of derivative time-series, wherein the neural network classifier is trained to detect disengagement motions and teleoperation motions of the first and second UIDs and generate either a disengagement decision or a teleoperation decision; and
   in response to receiving the disengagement decision from the neural network classifier, disengaging the first and second UIDs from controlling the first and second surgical tools.

20. The robotic surgical system of claim 19, wherein the plurality of derivative time-series include at least the velocities and accelerations of the first time-series and the second time-series, and wherein applying the neural network classifier on the plurality of derivative time-series allows for significantly reducing the data size required to make each disengagement or teleoperation decision, thereby expediting the speed of performing the real-time UID disengagement detections and preventing unintended movements of the surgical tools.

21. The robotic surgical system of claim 19, wherein the disengagement motions include docking motions of returning the first and second UIDs to respective docking stations.

* * * * *